United States Patent [19]
Shindo et al.

[11] Patent Number: 5,399,577
[45] Date of Patent: Mar. 21, 1995

[54] ISOXAZOLE DERIVATIVES AND SALTS THEREOF

[75] Inventors: Takashi Shindo, Tokushima; Naosuke Matsuura, Naruto; Naohiko Ono, Tokushima; Yushiro Akizawa, Itano; Kenji Nozaki; Masahiro Suzuki, both of Hanno, all of Japan

[73] Assignee: Taiho Pharmaceutical Co., Ltd., Tokyo, Japan

[21] Appl. No.: 140,020

[22] PCT Filed: May 1, 1992

[86] PCT No.: PCT/JP92/00571
§ 371 Date: Nov. 1, 1993
§ 102(e) Date: Nov. 1, 1993

[87] PCT Pub. No.: WO92/19604
PCT Pub. Date: Nov. 12, 1992

[30] Foreign Application Priority Data

May 1, 1991 [JP] Japan ................................. 3-100136

[51] Int. Cl.$^6$ ..................... A61K 31/42; A61K 31/44; C07D 261/08; C07D 213/16
[52] U.S. Cl. ..................................... 514/378; 514/340; 548/247; 548/248; 546/275
[58] Field of Search ................ 548/247, 248; 546/275; 514/378, 340

[56] References Cited

FOREIGN PATENT DOCUMENTS 0026928 10/1990 European Pat. Off. .
0549797 4/1994 European Pat. Off. .

OTHER PUBLICATIONS

Patent Abstracts of Japan, vol. 009, No. 211, 1990.
Patent Abstracts of Japan, vol. 014, No. 535, 1985.
Tetrahedron Letters No. 47, pp. 3495-3497 (1964).
CA 3842j 1,3-Dipolar . . . Ketones. L'Abbe et al., p. 313, 1974.
CA 118:254919s Preparation of . . . inhibitors. Shindo et al., p. 886, 1993.

*Primary Examiner*—Mary C. Lee
*Assistant Examiner*—Joseph K. McKane
*Attorney, Agent, or Firm*—Nikaido, Marmelstein, Murray & Oram

[57] ABSTRACT

An isoxazole derivative represented by the general formula (1) or a salt thereof:

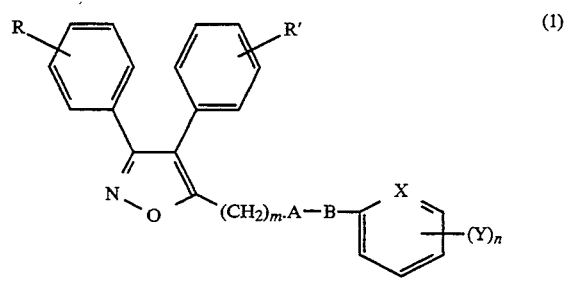

a method for preparing the same; compositions for inhibiting lipoxygenase and cyclooxygenase comprising an effective amount of the derivative and a pharmaceutically acceptable carrier therefor; and a method for inhibiting lipoxygenase and cyclooxygenase which comprises administering to a patient the derivative.

16 Claims, No Drawings

ISOXAZOLE DERIVATIVES AND SALTS THEREOF

This application is a 371 of PCT/JP92/00571 filed May 1, 1992.

TECHNICAL FIELD

The present invention relates to novel isoxazole derivatives having lipoxygenase inhibiting activity and cyclooxygenase inhibiting activity, salts thereof, and medical use thereof.

BACKGROUND ART

It is considered that leukotrienes produced by 5-lipoxygenase from arachidonic acid and prostaglandins produced by cyclooxygenase from arachidonic acid are deeply concerned in a crisis of allergic asthma, allergic rhinitis, inflammation, etc. Consequently it is desired to inhibit both 5-lipoxygenase and cyclooxygenase in order to strongly and properly inhibit various allergic diseases, inflammations and other diseases. The development of a drug inhibiting both enzymes is earnestly desired.

DISCLOSURE OF INVENTION

The present inventors have conducted a research in considering the foregoing problems in the background art, and found that novel isoxazole derivatives as indicated in the following formula (1) have an excellent lipoxygenase inhibiting activity and an excellent cyclooxygenase inhibiting activity, and are useful as a drug. Thus, the present invention has been accomplished.

The present invention provides isoxazole derivatives represented by the general formula (1) or a salt thereof:

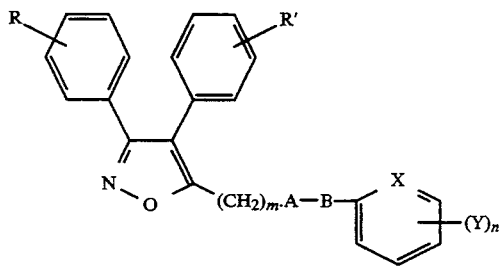

[wherein R and R' are the same or different and each is a hydrogen atom, a lower alkyl group, a lower alkoxy group or a halogen atom: m is 0 to 5; A is —NH—, —O— or a direct bond; B is —C(=Z)—NH—, —C(=Z)—(CH=CH)$_l$— or —CH=CH— (wherein Z is an oxygen or sulfur atom and l is 0 to 2); X is a nitrogen or carbon atom; n is 0 to 3; and Y is a hydroxy group, a lower alkoxy group, a lower alkyl group, a lower alkoxycarbonyloxy group, a lower alkoxycarbonylmethyloxy group, a carboxylmethyloxy group, an amino acid residue which may have a protective group, a lower alkylcarbonyloxy group, a pyridylcarbonyloxy group, a dimethylaminophenylcarbonyloxy group or a diloweralkyl phosphate residue; provided that when n is 2 or 3, the two or three Ys are the same or different and each is one of the groups mentioned above, that when n is 2 or more, two Ys may form a methylenedioxy group, that when X is a nitrogen atom, n is 0 and that when A is —NH—, m is 1 to 5].

The compounds of the present invention represented by the formula (1) has an excellent lipoxygenase inhibiting activity and cyclooxygenase inhibiting activity. Examples of lipoxygenases are 5-lipoxygenase, 12-lipoxygenase and 15-lipoxygenase, etc. The compounds of the invention exhibit, in particular, a potent activity of 5-lipoxygenase inhibition.

The compounds of the invention have excellent lipoxygenase inhibiting and cyclooxygenase inhibiting activities and are useful as antiasthmatic agents, antiallergic agents, agents for treating encephalopathy, cardiovascular agents, agents for treating nephritis, antiinflammatory analgesic agents, antirheumatic agents, agents for treating dermatosis such as psoriasis, and liver disease agents.

Accordingly, the present invention provides antiasthmatic agents, antiallergic agents, agents for treating encephalopathy, cardiovascular agents, agents for treating nephritis, antiinflammatory analgesic agents, antirheumatic agents, agents for treating dermatosis such as psoriasis, and liver disease agents, the agents each comprising an effective amount of a compound of the general formula (1) given above and a pharmaceutically acceptable carrier therefor.

The present invention also provides a method for treating asthma, allergy, encephalopathy, circulatory diseases, nephritis, inflammation, rheumatism, dermatosis such as psoriasis, and liver diseases which comprises administering an effective amount of a compound of the general formula (1) given above to patients.

The present invention is further concerned with the use of compounds of the general formula (1) given above in the treatment of asthma, allergy, encephalopathy, circulatory diseases, nephritis, inflammation, rheumatism, dermatosis such as psoriasis, and liver diseases.

Furthermore, the present invention is concerned with the use of compounds of the general formula (1) given above in preparing lipoxygenase inhibitor compositions.

Furthermore, the present invention is concerned with the use of compounds of the general formula (1) given above in preparing 5-lipoxygenase inhibitor compositions.

Furthermore, the present invention is concerned with the use of compounds of the general formula (1) given above in preparing cyclooxygenase inhibitor compositions.

Furthermore, the present invention is concerned with the use of compounds of the general formula (1) given above in inhibiting lipoxygenase.

Furthermore, the present invention is concerned with the use of compounds of the general formula (1) given above in inhibiting 5-lipoxygenase.

Furthermore, the present invention is concerned with the use of compounds of the general formula (1) given above in inhibiting cyclooxygenase.

In accordance with the invention, examples of the halogen atom represented by R and/or R' are a fluorine atom, a chlorine atom, a bromine atom and an iodine atom. Examples of the lower alkyl group represented by R, R' and/or Y are straight or branched alkyl groups having 1 to 4 carbon atoms, such as methyl, ethyl, n-propyl, isopropyl, n-butyl, isobutyl, sec-butyl and tert-butyl, and examples of the lower alkoxy group represented by R, R' and/or Y are straight or branched alkoxy groups having 1 to 4 carbon atoms, such as methoxy, ethoxy, n-propoxy, isopropoxy, n-butoxy, isobutoxy, sec-butoxy and tert-butoxy.

Examples of the lower alkoxycarbonyloxy group represented by Y are straight or branched alkoxycarbonyloxy groups having 2 to 7 carbon atoms, such as methoxycarbonyloxy, ethoxycarbonyloxy, n-propoxycarbonyloxy, isopropoxycarbonyloxy, n-butoxycarbonyloxy, isobutoxycarbonyloxy, sec-butoxycarbonyloxy, tert-butoxycarbonyloxy, pentyloxycarbonyloxy, isopentyloxycarbonyloxy, hexyloxycarbonyloxy, etc., and examples of the lower alkoxycarbonylmethyloxy group are straight or branched alkoxycarbonylmethyloxy groups having 3 to 8 carbon atoms, such as methoxycarbonylmethyloxy, ethoxycarbonylmethyloxy, n-propoxycarbonylmethyloxy, isopropoxycarbonylmethyloxy, n-butoxycarbonylmethyloxy, isobutoxycarbonylmethyloxy, sec-butoxycarbonylmethyloxy, tert-butoxycarbonylmethyloxy, pentyloxycarbonylmethyloxy, isopentyloxycarbonylmethyloxy, hexyloxycarbonylmethyloxy, etc.

The amino acid residue, which may have a protective group, represented by Y is a group derived from an amino acid by removal of the hydrogen atom of the carboxyl group thereof. Examples of said amino acid are natural or synthetic amino acids such as glycine, alanine, methionine, valine, serine, proline, leucine, isoleucine, glutamine, histidine, phenylalanine and phenylglycine, and examples of the protective group for the amino group of the amino acid are lower alkyl groups having 1 to 6 carbon atoms, lower acyl groups having 2 to 5 carbon atoms, lower alkoxycarbonyl groups having 2 to 5 carbon atoms and a benzyloxycarbonyl group, among others. Examples of the amino acid having a protective group, are N,N-dimethylglycine, N-acetylglycine, N-tert-butoxycarbonylglycine, N-benzyloxycarbonylglycine, N-acetylvaline, N-tert-butoxycarbonylvaline.

Examples of the lower alkylcarbonyloxy group represented by Y are straight or branched alkylcarbonyloxy groups having 2 to 5 carbon atoms, such as methylcarbonyloxy, ethylcarbonyloxy, n-propylcarbonyloxy, isopropylcarbonyloxy, n-butylcarbonyloxy, isobutylcarbonyloxy, sec-butylcarbonyloxy and tert-butylcarbonyloxy, and examples of the diloweralkyl phosphate residue are phosphoric acid residues substituted with two alkyl groups having 1 to 4 carbon atoms, such as the dimethyl phosphate residue, diethyl phosphate residue, dipropyl phosphate residue and dibutyl phosphate residue, in particular groups of the formula —O—P(O)(OR$^o$)$_2$ (wherein R$^o$ is an alkyl group having 1 to 4 carbon atoms).

Examples of the salts of the isoxazole compounds of the invention include basic group-derived salts, such as inorganic acid salts, such as hydrochloride, sulfate, nitrate, phosphate, etc. and organic acid salts, such as maleate, succinate, malate, fumarate, p-toluenesulfonate, methanesulfonate, etc., and acid group-derived salts, such as sodium salt, potassium salt calcium salt, etc.

Among the compounds of general formula (1) mentioned above, those in which R and R' are the same or different and each is a hydrogen atom, a lower alkyl group, a lower alkoxy group or a halogen atom are preferred and those in which R and R' are the same or different and each is a lower alkoxy group or a halogen atom are more preferred.

In preferred embodiments, m is 0 to 3, A is —NH— or a direct bond, B is —C(=Z)—(CH=CH)$_l$— (wherein Z is an oxygen or sulfur atom and l is 1 or 2), Y is a hydroxy group, a lower alkoxy group, a lower alkyl group or a lower alkoxycarbonyloxy group, n is 2 or 3, and X is a carbon atom. In particular, in more preferred embodiments, m is 1 to 3.

Preferred among the compounds of general formula (1) mentioned above are those compounds in which R and R' are the same or different and each is a hydrogen atom, a lower alkyl group, a lower alkoxy group or a halogen atom, m is 0 to 3, A is —NH— or a direct bond, B is —C(=Z)—(CH=CH)$_l$— (wherein Z is an oxygen or sulfur atom and l is 1 or 2), Y is a hydroxy group, a lower alkoxy group, a lower alkyl group or a lower alkoxycarbonyloxy group, n is 2 or 3, and X is a carbon atoms.

Most preferred are those compounds in which R and R' are the same or different and each is a lower alkoxy group or a halogen atom, m is 1 to 3, A is —NH— or a direct bond, B is —C(=Z)—(CH=CH)$_l$— (wherein Z is an oxygen or sulfur atom and l is 1 or 2), Y is a hydroxy group, a lower alkoxy group, a lower alkyl group or a lower alkoxycarbonyloxy group, n is 2 or 3, and X is a carbon atom.

The compounds of the present invention as represented by general formula (1) can be produced by the methods shown below in terms of reaction formulas (i) to (vii).

<Reaction formula (i)>

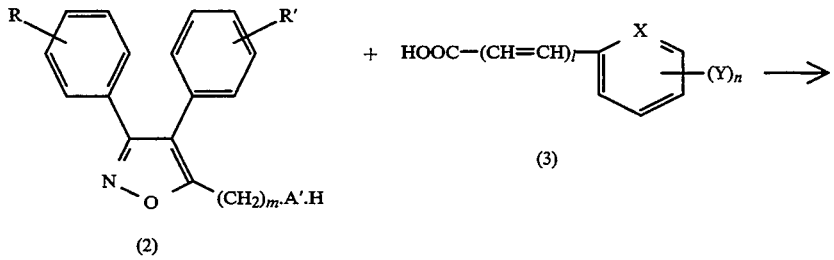

<Reaction formula (i)>

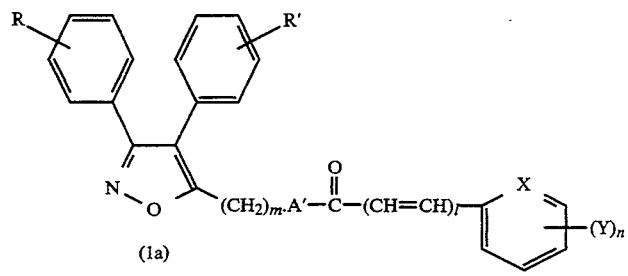

[In the above formula, R, R', m, Y, X and n are as defined above, A' is —O— or —NH— and l is 1 or 2.]

The desired isoxazole derivatives of general formula (1a) can be produced by reacting an alcohol or amine of general formula (2) with a carboxylic acid of general formula (3) in a solvent, using a condensing agent, where appropriate in the presence of a catalyst. In cases where Y in the compound of general formula (3) is a hydroxy group, the condensation may be carried out after protection of said group with an appropriate protective group. The protective group is not limited to any particular species provided that the subsequent deprotection reaction for the elimination thereof will not produce any adverse effect. Thus, methoxyethoxymethyl, methoxymethyl, tetrahydrofuranyl, tetrahydropyranyl and like groups can be used and introduction of these protective groups can be performed by the method described in the Journal of the American Chemical Society, 100, 8031 (1978). The solvent mentioned above is not limited to any particular species provided that it is inert to the reaction. Thus, use may be made of, for example, ethers such as diethyl ether, tetrahydrofuran, etc., halogenated hydrocarbons such as methylene chloride, chloroform, etc., aromatic hydrocarbons such as benzene, toluene, etc., and aprotic polar solvents such as N,N-dimethylformamide, dimethyl sulfoxide, acetonitrile, etc. As examples of the condensing agent, there may be mentioned N,N-dicyclohexylcarbodiimide, ethyl chlorocarbonate, pivaloyl chloride and chlorosulfonyl isocyanate, among others. The catalyst is, for example, 4-dimethylaminopyridine, 1-hydroxybenzotriazole, pyridine or triethylamine. In carrying out the reaction, the compound of general formula (3) is used preferably in an amount of about 1 to 2 equivalents, the condensing agent in an amount of about 1 to 3 equivalents, and the catalyst in an amount of about 0.1 to 2 equivalents, relative to the compound of general formula (2). The reaction temperature is within the range of ice cooling to around room temperature, and the reaction time is within the range of about 1 to 48 hours. These conditions are favorable to the progress of the reaction.

<Reaction formula (ii)>

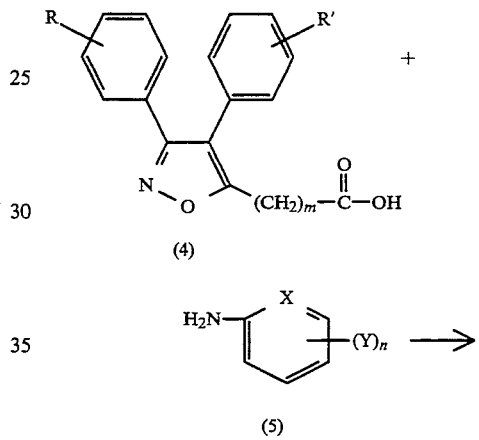

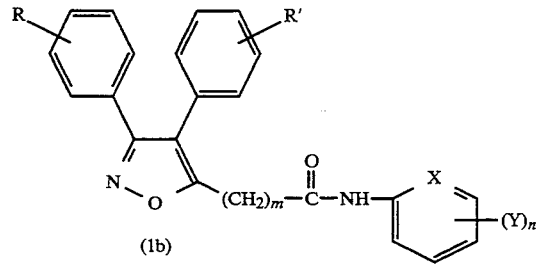

[In the above formula, R, R', m, Y, X and n are as defined above.]

The objective isoxazole derivative of general formula (1b) can be produced by reacting a carboxylic acid of general formula (4) with an amine of general formula (5) in a solvent, using a condensing agent, when appropriate in the presence of a catalyst. In cases where Y in the compound of general formula (5) is a hydroxy group, said group may be protected prior to the condensation, as in the method represented by reaction formula (i). As said solvent and catalyst, use may be made, for instance, of those specifically mentioned above in relation to the reaction formula (i). The condensing agent includes those specifically mentioned above in relation to the reaction formula (i) and, further, 1,3-thiazolidine-2-thione and the like. When carried out under the same reaction conditions as mentioned above for the reaction formula (i), the reaction proceeds advantageously.

<Reaction formula (iii)>

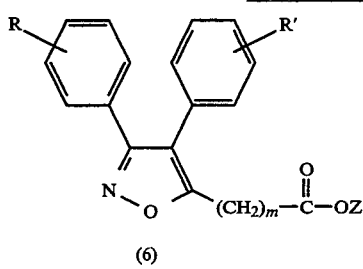
(6)

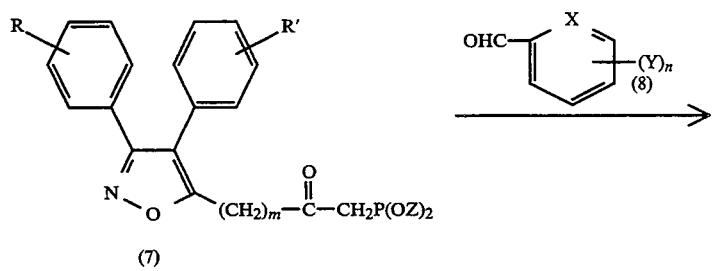
(7)

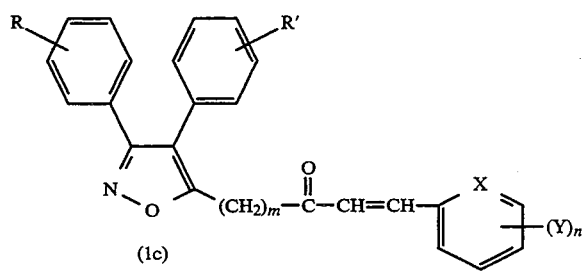
(1c)

[In the above formula, R, R', m, Y, X and n are as defined above and Z is a methyl or ethyl group.]

The compound of general formula (7) can be prepared by stirring a dialkyl methylphosphonate and n-butyllithium in a solvent at −78° C. or below under a nitrogen atmosphere for 10 to 30 minutes and then adding an ester of general formula (6) to the solution. Said solvent is not limited to any particular species provided it is inert to the reaction. Thus, ethers such as diethyl ether, tetrahydrofuran, etc. may be mentioned as examples thereof. In carrying out the reaction, the dialkyl methylphosphonate and n-butyllithium are preferably used each in an amount of about 1 to 5 equivalents relative to the compound of general formula (6). For advantageous progress of the reaction, the reaction temperature is within the range of about −78° C. to ice cooling and the reaction time within the range of about 30 minutes to about 2 hours. The dialkyl methylphosphonate is dimethyl methylphosphonate or diethyl methylphosphonate, for instance.

Then, the thus-obtained compound of general formula (7) is reacted with sodium hydride in a solvent with ice cooling for 30 minutes to 1 hour, an aldehyde of general formula (8) is then added and the reaction is carried out with ice cooling or at around room temperature to give the objective isoxazole derivative of general formula (1c). Said solvent may be any of the solvents recommended above for use in the synthesis of the compound (7). In cases where Y in the compound of general formula (8) is a hydroxy group, said group may be protected prior to the condensation, as in the method represented by the reaction formula (i) given hereinabove. In carrying out the reaction, sodium hydride and the compound of general formula (8) are preferably used each in an amount of about 1 to 2 equivalents relative to the compound of general formula (7).

<Reaction formula (iv)>

(4) + (8) ⟶

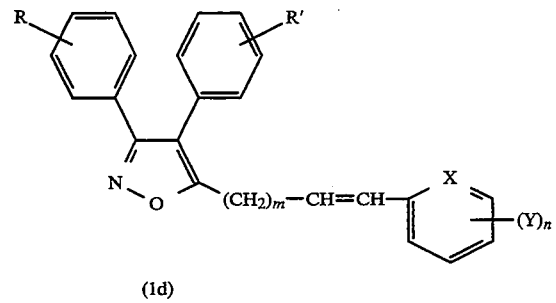
(1d)

[In the above formula, R, R', m, Y, X and n are as defined above.]

The objective isoxazole derivative of general formula (1d) can be produced by reacting a carboxylic acid of general formula (4) with an aldehyde of general formula (8) in a solvent, or without using any solvent, in the presence of a base. Said solvent may be any of the solvents specifically shown above in relation to the reaction formula (i) or may be an alcohol such as ethanol. The base includes organic amines such as piperidine, pyridine, etc. In carrying out the reaction, the compound of general formula (8) is preferably used in an amount of about 1 to 1.5 equivalents, and the base in an amount of about 1 to 2 equivalents, relative to the compound of general formula (4). For advantageous progress of the reaction, the reaction temperature is the refluxing temperature of the solvent or, when no solvent is used, about 100° to 150° C., and the reaction time is about 2 to 5 hours. The conditions for the reaction illustrated by the above reaction formula (iv) are not limited to those mentioned above but those conditions generally known for the Knoevenagel reaction may be employed for the production of the desired isoxazole derivative of general formula (1d).

temperature is within the range of about −78° C. to room temperature and the reaction time within the range of about 6 to 12 hours.

The thus-obtained compound of general formula (10) is then treated in the same manner as in the method shown by the reaction formula (iv) to give the desired isoxazole derivative of general formula (1e).

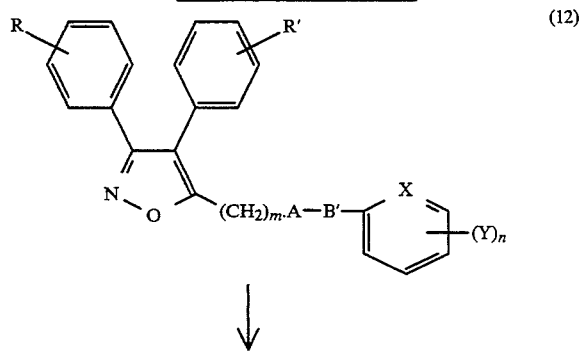

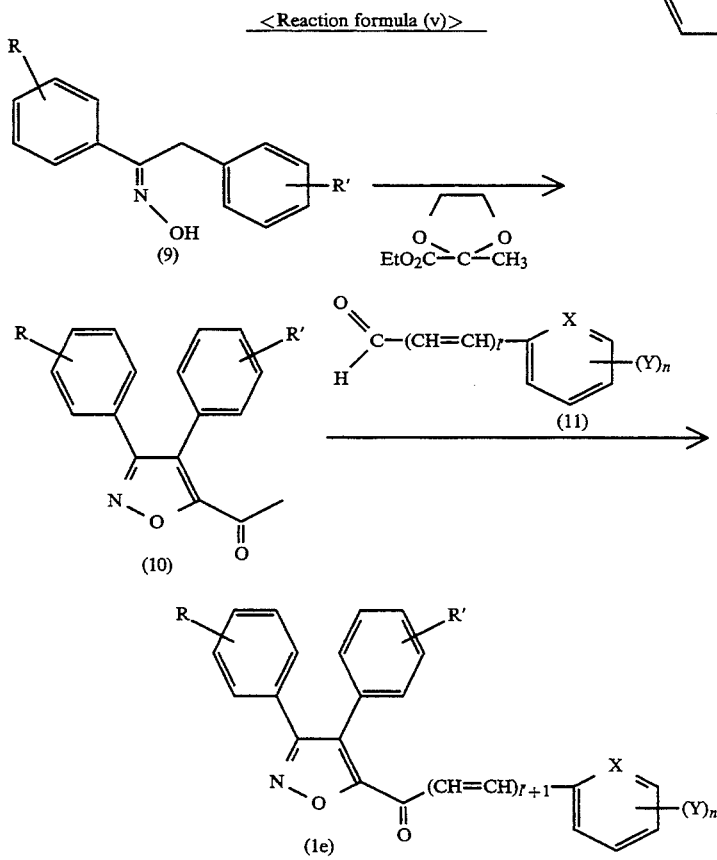

[In the above formula, R, R', Y, X and n are as defined above and l' is 0 or 1.]

A compound of general formula (10) is prepared by reacting a compound of general formula (9) with an alkyllithium or phenyllithium and then reacted with ethyl 1,3-dioxolane-2-methyl-2-carboxylate, which is already known in the art, followed by reaction with an acid in a solvent. The solvent is not limited to any particular species provided that it is inert to the reaction. Thus, the solvent includes, among others, ethers such as ethyl ether, tetrahydrofuran, etc. and saturated alkyls such as hexane and cyclohexane. The alkyllithium is, for example, methyllithium, n-butyllithium, sec-butyllithium, tert-butyllithium, etc. Usable as the acid are inorganic acids such as hydrochloric acid, sulfuric acid, etc. and organic acids such as p-toluenesulfonic acid, etc. For advantageous progress of the reaction, the alkyllithium or phenyllithium is preferably used in an amount of 2 to 3 equivalents relative to the compound of general formula (9), the acid is added in an amount sufficient to make the liquid reaction mixture acidic, and the reaction is carried out preferably under an inert dry gas atmosphere such as nitrogen or argon. The reaction -continued
<Reaction formula (vi)>

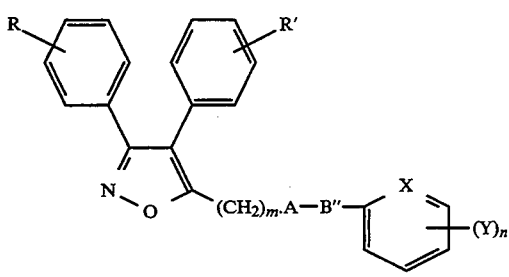

[In the above formula, R, R', m, A, Y, X and n are as defined above, B' is —CONH— or —CO—(CH=CH-)$_l$—, and B" is —CSNH— or —CS—(CH=CH)$_l$— (wherein l is as defined above).]

The objective isoxazole derivative of general formula (1f) can be produced by reacting a compound of general formula (12) with Lawesson's reagent in a solvent. Said solvent is not limited to any particular species provided that it is inert to the reaction. Thus, for instance, ethers such as ethyl ether, tetrahydrofuran, etc., aromatic hydrocarbons such as benzene, toluene, etc., and halogenated hydrocarbons such as chloroform, methylene chloride, etc. can be used. In carrying out the invention, Lawesson's reagent is preferably used in an amount of about 1 to 2 equivalents relative to the compound of general formula (12). For advantageous progress of the reaction, the reaction temperature is within the range of about room temperature to around the boiling point of the solvent and the reaction time within the range of about 1 to 6 hours.

<Reaction formula (vii)>

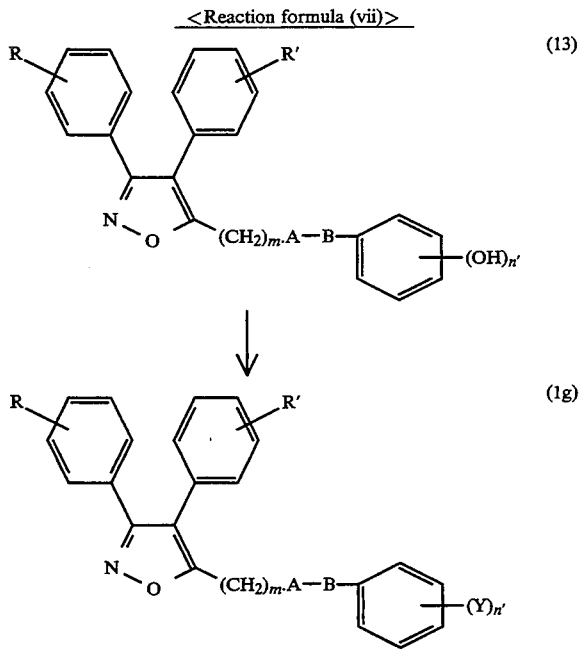

[In the above formula, R, R', m, A and B are as defined above, n' is an integer of 1 to 3 and Y' is a lower alkoxycarbonyloxy group, a lower alkoxycarbonylmethyloxy group, an amino acid residue which may optionally have a protective group, a lower alkylcarbonyloxy group, a pyridylcarbonyloxy group; a dimethylaminophenylcarbonyloxy group or a di-lower alkyl phosphate residue.]

The objective isoxazole derivative of general formula (1g) can be produced by reacting a compound of general formula (13) with a lower alkoxycarbonyl chloride (a lower alkyl chlorocarbonate), a lower alkyl α-haloacetate, an amino acid or an N-protected amino acid, a lower fatty acid or a lower fatty acid chloride, nicotinic acid, isonicotinic acid, dimethylamino benzoic acid or a di-lower alkylphosphoryl chloride in an appropriate solvent in the presence of a condensing agent.

Examples of the lower alkoxycarbonyl chloride are an alkoxycarbonyl chloride having 2 to 5 carbon atoms, such as methoxycarbonyl chloride, ethoxycarbonyl chloride, n-propoxycarbonyl chloride, isopropoxycarbonyl chloride, n-butoxycarbonyl chloride, isobutoxycarbonyl chloride, sec-butoxycarbonyl chloride or tert-butoxycarbonyl chloride.

Examples of the lower alkyl α-haloacetate is, for example, methyl chloroacetate, methyl bromoacetate, ethyl chloroacetate, ethyl bromoacetate, propyl bromoacetate, or butyl bromoacetate.

Examples of the amino acid are natural and synthetic amino acids, such as glycine, alanine, methionine, valine, serine, proline, leucine, isoleucine, glutamine, histidine, phenylalanine and phenylglycine. Generally, however, the N-protected amino acid mentioned above, with its amino group protected, is preferred. The protective group may be any of those amino-protecting groups specifically mentioned above.

Examples of the lower fatty acid includes straight or branched fatty acids having 2 to 5 carbon atoms, such as acetic acid, propionic acid, butyric acid, isobutyric acid, valeric acid, isovaleric acid, pivalic acid, etc., and examples of the acid chloride thereof are straight or branched acid chlorides having 2 to 5 carbon atoms, such as acetyl chloride, propionyl chloride, butyryl chloride, isobutyryl chloride, valery chloride, isovaleryl chloride and pivaloyl chloride.

As examples of the di-lower alkylphosphoryl chloride, there may be mentioned di-($C_1$-$C_4$ alkyl)phosphoryl chlorides such as dimethyl chlorophosphate, diethyl chlorophosphate, dipropyl chlorophosphate and dibutyl chlorophosphate.

The solvent is not limited to any particular species provided that it is inert to the reaction. Thus, use may be made of ethers such as diethyl ether, tetrahydrofuran, etc. halogenated hydrocarbons such as methylene chloride, chloroform, etc., aromatic hydrocarbons such as benzene, toluene, etc., and aprotic polar solvents such as N,N-dimethylformamide, dimethyl sulfoxide, etc. As regards the condensing agent, those commonly used in peptide synthesis, such as N,N'-dicyclohexylcarbodiimide and ethoxycarbonyl chloride, can be used when the reactant is an N-protected amino acid, a lower fatty acid, nicotinic acid, isonicotinic acid or 4-dimethylaminobenzoic acid. In this case, an additive, such as an organic amine, for example N,N-di methylaminopyridine or 1-hydroxybenzotriazole, may be used, when necessary. The use of such additive may advantageously promote the progress of the reaction. In the reaction with a lower alkoxycarbonyl chloride, a lower alkyl α-haloacetate, a lower fatty acid chloride or a di-lower alkylphosphoryl chloride, a base can generally be used as the condensing agent and, as examples of said base, there may be mentioned organic bases such as pyridine, triethylamine, etc., and inorganic bases such as sodium hydrogen carbonate, potassium hydrogen carbonate, sodium carbonate, potassium carbonate, sodium hydride, etc. As for the proportions of the reactants, the lower alkoxycarbonyl chloride (lower alkyl chlorocarbonate), lower alkyl α-haloacetate, amino acid or N-protected amino acid, lower fatty acid, lower fatty acid chloride, nicotinic acid, isonicotinic acid, dimethylaminobenzoic acid or di-lower alkylphosphoryl chloride is recommendably used in an amount of about 1 to 2.5 equivalents, and the condensing agent in an amount of about 1 to 2.5 equivalents, relative to the compound of general formula (13). When using the organic amines mentioned above as additives, the organic amine is used in an amount of about 1–2.5 equivalents relative to the compound of general formula (13). The reaction will be complete when carried out at a temperature within the range of ice cooling to around room temperature for a period of about 1 to 15 hours. In cases where an N-protected amino acid is used, deprotection may be carried out in a conventional manner when necessary. Usable as the deprotecting agent are conventional ones, for example inorganic acids such as hydrochloric acid, sulfuric acid, etc., and organic acids such as p-toluenesulfonic acid, trifluoroacetic acid, formic acid, etc. As regards the deprotection conditions, those conditions well known in the art for ordinary peptide synthesis can be employed.

The compound of the general formula (2) to be used as the starting material in the process illustrated above by reaction formula (i), more specifically including compounds (19), (21), (23) and (26), can be prepared, for example, by following one of the reaction formulas (viii), (ix) and (x) shown below.

<Reaction formula (viii)>

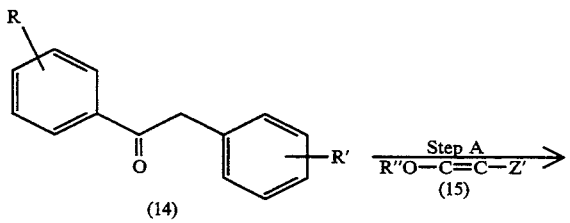

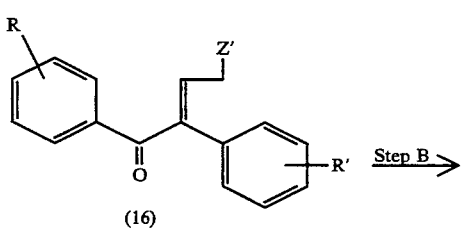

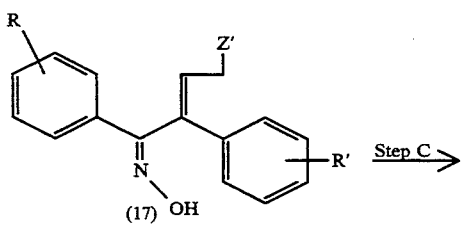

-continued
<Reaction formula (viii)>

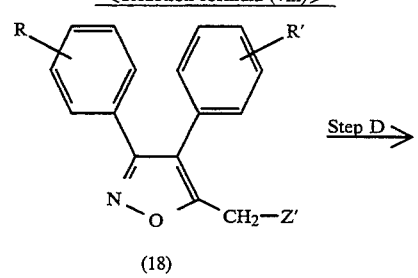

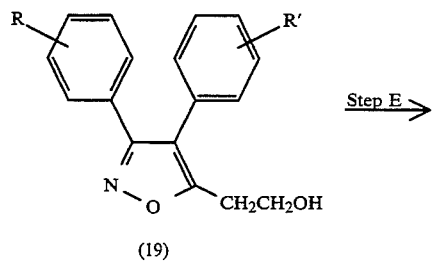

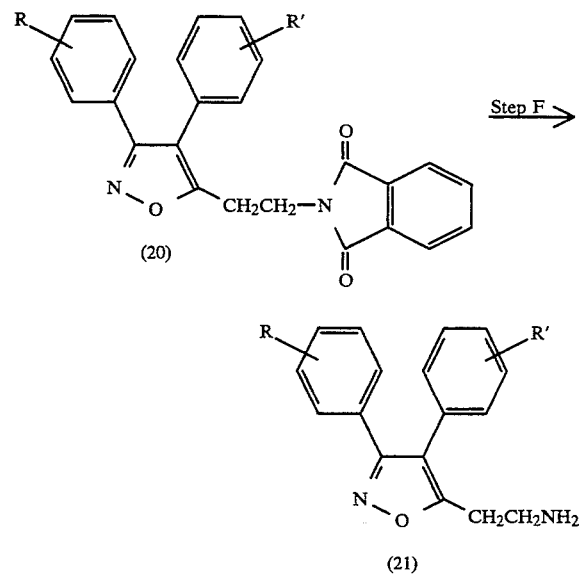

[In the above formula, R and R' are as defined above, R" is a lower alkyl group and Z' is a lower alkoxycarbonyl group or a nitrile group.]

Step A

A compound of general formula (16) is prepared by reacting a deoxybenzoin derivative of general formula (14) with an alkoxyacrylonitrile or alkoxyacrylic acid derivative of general formula (15) in an appropriate solvent in the presence of a base.

As the lower alkyl group represented by R", there may be mentioned those lower alkyl groups specifically mentioned hereinabove. Examples of the lower alkoxycarbonyl group represented by Z' are straight or branched lower alkoxycarbonyl groups having 2 to 5 carbon atoms, such as methoxycarbonyl, ethoxycarbonyl, n-propoxycarbonyl, isopropoxycarbonyl, n-butoxycarbonyl, isobutoxycarbonyl, tert-butoxycarbonyl, etc.

Examples of said solvent are alcohols such as methanol, ethanol, tert-butanol, etc., ethers such as diethyl ether, tetrahydrofuran, etc., aromatic hydrocarbons such as benzene, toluene, etc., halogenated hydrocarbons such as carbon tetrachloride, chloroform, etc., and nonpolar aprotic solvents such as N,N-dimethylformamide, dimethyl sulfoxide, etc. Examples of the base are strong bases such as sodium hydroxide, potassium hydroxide, sodium hydride, sodium amide, sodium methoxide, potassium tert-butoxide, butyllithium, etc., and organic bases such as triethylamine, diethylaminopyridine, pyridine, etc. As regards the proportions of the reactants, the compound of general formula (15) is preferably used in an amount of about 1 to 3 equivalents, and the base in an amount of about 0.1 to 3 equivalents, relative to the compound of general formula (14). For advantageous progress of the reaction, the reaction temperature is within the range of ice cooling to around the boiling point of the solvent, and the reaction time is about 0.5 to 20 hours.

Step B

The compound of general formula (16) as obtained in step A is reacted with hydroxylamine or a salt thereof in an appropriate solvent to give a compound of general formula (17). The salt of hydroxylamine to be submitted to the reaction is not limited to any particular species but includes the hydrochloride and sulfate that are commercially available, for instance. The solvent is not limited to any particular species provided that it is inert to the reaction. Thus, for example, those specifically mentioned in relation to step A may be used. Hydroxylamine or a salt thereof is preferably used in an amount of about 1 to 10 equivalents relative to the compound of general formula (16). For advantageous progress of the reaction, the reaction temperature is about room temperature to the boiling point of the solvent and the reaction time is about 1 to 30 hours. In carrying out the reaction, an acid or base may be added as necessary. Further, the reaction may be carried out in a mixed solvent such as a buffer solution.

Step C

The compound of general formula (17) is subjected to cyclization in an appropriate solvent using a halogenating agent or the like or to reaction with an oxidizing agent in an appropriate solvent or without solvent to give a compound of general formula (18). The solvent is not particularly limited provided that it is inert to the reaction. Thus, for example, those solvents specifically mentioned in relation to step A may be used. Acetic acid or the like may also be used. The halogenating agent to be used in the cyclization reaction is, for example, chlorine, bromine, iodine, N-chlorosuccinimide or N-bromosuccinimide. The halogenating agent is preferably used in an amount of about 1 to 3 equivalents relative to the compound of general formula (17). For advantageous progress of the reaction, the reaction temperature is about $-70°$ to $150°$ C. and the reaction time is about 1 to 24 hours.

As specific examples of the oxidizing agent, there may be mentioned oxides such as potassium permanganate, manganese dioxide, potassium periodate, etc., metal salts such as lead tetraacetate, mercury acetate, etc., an peroxides such as hydrogen peroxide, peracetic acid, etc. In addition to the method using these oxidizing reagents, oxygen oxidation methods using air or oxygen or organic electrolytic oxidation methods utilizing anodic oxidation, for instance, can also give the compound of general formula (18).

In the reaction using an oxidizing agent, the oxidizing agent is preferably used in an amount of about 0.2 to 10 equivalents relative to the compound of general formula (17). For advantageous progress of the reaction, the reaction temperature is within the range of ice cooling to about $100°$ C. and the reaction time within the range of about 5 minutes to about 10 hours.

In the oxygen oxidation and organic electrolytic oxidation methods, a reaction temperature of about $-20°$ C. to about $100°$ C. and a reaction period of about 5 minutes to about 10 hours are favorable for the progress of the reaction. It is generally known that these reactions can proceed efficiently in the presence of a catalyst. The catalyst is preferably used in an amount of about $1 \times 10^{-5}$ to 10 equivalents relative to the compound of general formula (17). Examples of the catalyst are metals such as cobalt, rhodium, palladium, copper, cerium, ruthenium, etc., and metal compounds such as metal salts, metal oxides, metal complexes, etc.

Step D

A compound of general formula (18) in which Z' is a nitrile group is subjected to solvolysis or hydrolysis in the presence of an acid or base to give a corresponding carboxylic acid, which is esterified and further reduced to give a compound of general formula (19). The solvolysis or hydrolysis can be effected by the solvolysis method described in Japanese Unexamined Patent Publication No. 60-75471 or by a hydrolysis method conventional in the relevant field of art. The acid to be used in the solvolysis or hydrolysis reaction includes inorganic acids such as hydrochloric acid, sulfuric acid, nitric acid, etc. and the base includes inorganic bases such as sodium hydroxide, potassium hydroxide, sodium carbonate, etc. The esterification can be carried out by a method conventional in the relevant field of art, for example in an alcohol solvent such as methanol or ethanol using an acid as a catalyst. Said acid is, for example, an inorganic acid such as hydrochloric acid or sulfuric acid, or an organic acid such as p-toluenesulfonic acid.

The reduction of the ester can be carried out in an appropriate solvent using a reducing agent. The solvent may be any of those solvents specifically mentioned in relation to step A. The reducing agent is, for example, lithium aluminum hydride, sodium borohydride or the like. The reducing agent is preferably used in an amount of about 1 to 10 equivalents relative to the ester. For advantageous progress of the reaction, the reaction temperature is within the range of ice cooling to around room temperature and the reaction time is about 10 minutes to about 24 hours.

A compound of general formula (18) in which Z' is a lower alkoxycarbonyl group, when subjected to reduction in the same manner as mentioned above, gives a compound of general formula (19).

The intermediate (Z' being carboxy) in this process can also be prepared by the method described in Japanese Unexamined Patent Publication No. 56-59764.

Step E

The alcohol of general formula (19), when reacted with phthalimide, triphenylphosphine and diethyl azodicarboxylate in an appropriate solvent, gives a compound of general formula (20). As the solvent, there may be mentioned ethers such as diethyl ether, tetrahydrofuran, etc., halogenated hydrocarbons such as methylene chloride, chloroform, etc., and aromatic hydrocarbons such as benzene, toluene, etc.

Preferably, phthalimide, triphenylphosphine and diethyl azodicarboxylate are used each in an amount of about 1 to 2 equivalents relative to the alcohol of general formula (19). For advantageous progress of the reaction, the reaction temperature is within the range of ice cooling to around room temperature and the reaction time is about 1 to 48 hours.

Step F

The compound of general formula (20) is treated under the conditions generally employed for the Gabriel reaction to give a compound of general formula (21). For advantageous progress of the reaction, hydrazine hydrate is used in an amount of about 1 to 1.1 equivalents relative to the compound of general formula (20) and the reaction is carried out in an ethanol solvent at room temperature to the vicinity of the boiling point of ethanol for about 1 to 24 hours.

The objective amine can also be prepared by conventional acid or alkali hydrolysis.

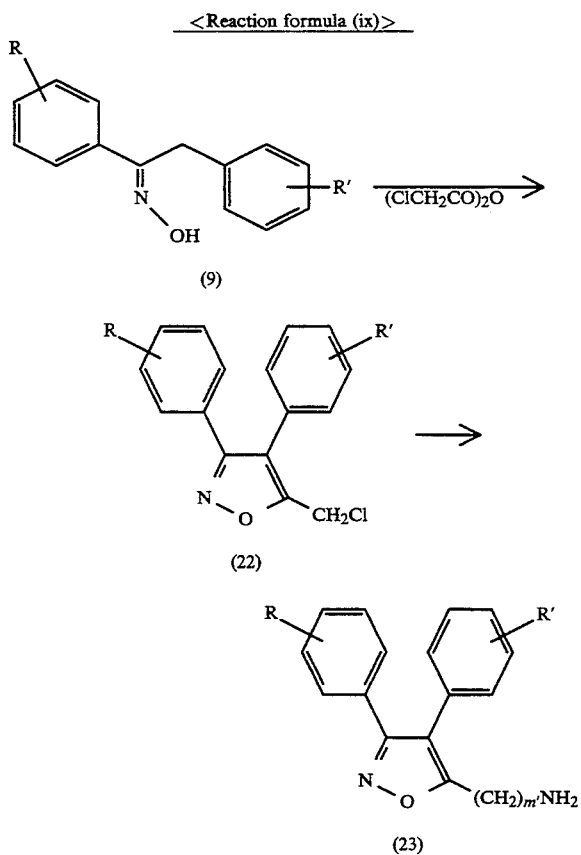

[In the above formula, R and R' are as defined above and m' is an integer of 1 to 5.]

A compound of general formula (9) is reacted with an alkyllithium or phenyllithium and then reacted with an ω-chloro-lower fatty acid anhydride such as bis(chloroacetic) anhydride or bis(chloropropionic) anhydride to give a compound of general formula (22). The solvent is not limited to particular species but includes ethers such as ethyl ether, tetrahydrofuran, etc., and saturated alkyls such as hexane and cyclohexane. The alkyllithium is, for example, methyllithium, n-butyllithium, sec-butyllithium or tert-butyllithium. For advantageous progress of the reaction, the alkyllithium or phenyllithium is used in an amount of about 2 to 3 equivalents, and the ω-chloro-lower fatty acid anhydride in an amount of about 1 to 2 equivalents, relative to the compound of general formula (9), and the reaction is carried out preferably under an inert dry gas atmosphere such as nitrogen or argon. For advantageous progress of the reaction, the reaction temperature is about −20° C. to around room temperature and the reaction is about 1 to 2 hours for the reaction with the alkyllithium or phenyllithium and about 0.5 to 2 hours for the reaction with chloroacetic anhydride.

The thus-obtained compound of general formula (22) is then reacted with ammonia in a solvent to give a compound of general formula (23). The solvent is not specifically limited provided that it is inert to the reaction. Thus, for example, alcohols such as methanol, ethanol, etc., and water may be used. Ammonia is used in the form of gaseous ammonia to be passed through the solvent mentioned above or in the form of aqueous ammonia. For advantageous progress of the reaction, ammonia is used in excess relative to the compound of general formula (22) and the reaction is carried out at a temperature approximately within the range of room temperature to the boiling point of the solvent for a period of about 2 to 12 hours.

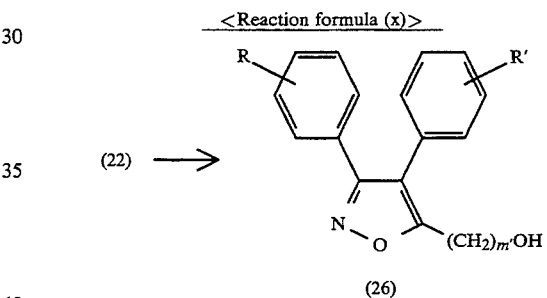

[In the above formula, R, R' and m' are as defined above.]

A compound of general formula (22) is reacted with an inorganic base in a solvent to give a compound of general formula (26). The solvent is, for example, an alcohol such as methanol or ethanol, or water, or a mixture of these. Such a solvent as tetrahydrofuran may further be used as a cosolvent. The inorganic base is, for example, sodium hydroxide, potassium hydroxide, potassium carbonate, sodium carbonate or calcium oxide. In carrying out the reaction, the inorganic base is preferably used in an amount of about 1 to 3 equivalents relative to the compound of general formula (22). For advantageous progress of the reaction, the reaction temperature is approximately within the range of room temperature to the boiling point of the solvent and the reaction time is about 1 to 6 hours.

The compounds of general formulas (4) and (6) to be used as the starting materials in the processes shown above in terms of reaction formulas (ii) to (iv) can be prepared, for example, by the process shown below in terms of reaction formula (Xi).

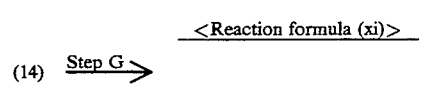

-continued

<Reaction formula (xi)>

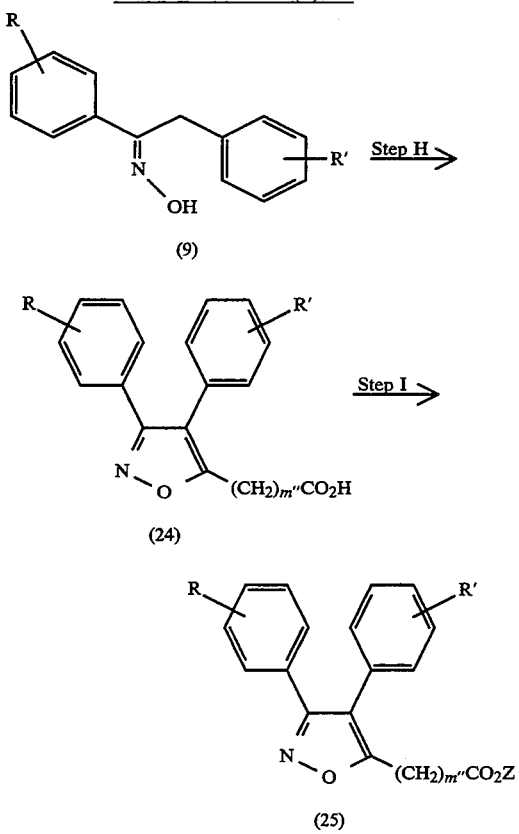

[In the above formula, R, R' and Z are as defined above. and m" is an integer of 2 to 5.]

Step G

A compound of general formula (9) can be prepared by the same oxime formation method as in the above mentioned step B in reaction formula (viii).

Step H

The compound of general formula (9) is reacted with an alkyllithium or phenyllithium in a solvent and further reacted with an acid anhydride to give a carboxylic acid of general formula (24). The solvent mentioned above is not specifically limited provided that it is inert to the reaction. Thus, use may be made of ethers such as ethyl ether, tetrahydrofuran, etc., saturated alkyls such as hexane, cyclohexane, etc., and halogenated hydrocarbons such as chloroform, methylene chloride, etc., among others. The alkyllithium is, for example, methyllithium, n-butyllithium, sec-butyllithium or tert-butyllithium. The acid anhydride is, for example, succinic anhydride, glutaric anhydride, adipic anhydride, heptanedioic anhydride or the like. For advantageous progress of the reaction, the alkyllithium or phenyllithium is used in an amount of about 2 to 3 equivalents, and acid anhydride in an amount of about 1-2 equivalents relative to the compound of general formula (9) and the reaction is carried out preferably under an inert dry gas atmosphere such as nitrogen or argon. For advantageous progress of the reaction the reaction temperature is about −20° C. to around room temperature and the reaction time is about 1 to 2 hours for the reaction with the alkyllithium or phenyllithium and about 0.5 to 2 hours for the reaction with the acid anhydride.

Step I

A compound of general formula (25) can be prepared in the same manner of esterification as used above in Step D in reaction formula (viii).

It is also possible to convert the compounds of general formulas (24) and (25) as obtained in accordance with reaction formula (xi) to the corresponding compounds of general formula (2) by treating in the same manner as illustrated in reaction formula (viii).

The thus-obtained compound of the invention, when it has a basic group, can be converted to a salt form based on the basic group by a conventional method, for example by reacting with an inorganic or organic acid such as mentioned above in a solvent such as an ether, a lower alcohol, ethyl acetate or hexane at a temperature around room temperature. When the compound of the invention obtained has an acidic group, said compound can be converted to a salt form based on said acidic group in the conventional manner, for example by reacting with an alkali metal or alkaline earth metal hydroxide such as sodium hydroxide, potassium hydroxide or calcium hydroxide, or a strong base such as sodium ethoxide, potassium ethoxide or sodium hydride, in lieu of the inorganic or organic acid mentioned above, in such a solvent as mentioned above.

The compounds produced in any of the above-mentioned reaction formulas (i) to (xi) can be isolated and purified by means generally employed in the relevant field of art, for example by concentration, filtration, recrystallization, various chromatographic techniques and so forth.

For use as medicaments, the compounds of the present invention can be made into various pharmaceutical dosage forms according to a preventive or therapeutic purpose. Examples of pharmaceutical dosage forms are oral preparations, injections, suppositories, ointments, plasters and so on. Such preparations can be formulated in a manner already known or conventional to those skilled in the art.

For the formulation of solid preparations for oral administration, an excipient and, when required, a binder, disintegrator, lubricant, coloring agent, corrigent, flavor, etc. are added to the compound of the invention, and then a preparation is formulated in a usual way as tablets, coated tablets, granules, powders, capsules, or the like. Such additives are those already known in the art, and useful examples are excipients such as lactose, sucrose, sodium chloride, glucose, starch, calcium carbonate, kaolin, microcrystalline cellulose and silicic acid; binders such as water, ethanol, propanol, simple syrup, glucose solutions, starch solution, gelatin solution, carboxymethyl cellulose, hydroxypropyl cellulose, hydroxypropyl starch, methyl cellulose, ethyl cellulose, shellac, calcium phosphate and polyvinyl pyrrolidone; disintegrators such as dried starch, sodium alginate, agar powder, sodium hydrogen carbonate, calcium carbonate, sodium lauryl sulfate, stearic acid monoglyceride and lactose; lubricants such as purified talc, stearic acid salt, borax and polyethylene glycol; corrigents such as sucrose, bitter orange peel, citric acid and tartaric acid, etc.

For the formulation of liquid preparations for oral administration, a corrigent, buffer, stabilizer, flavor, etc. can be added to the compound of the present invention, and the mixture can be formulated in a usual way into an oral liquid preparations, syrup, elixir or the like. Examples of useful corrigents are those exemplified above. Examples of buffers are sodium citrate, etc. Examples of stabilizers are tragacanth, gum arabic, gelatin, etc.

Injections can be prepared as a subcutaneous, intramuscular or intravenous injection in a conventional way by adding to the compound of the invention a pH adjusting agent, buffer, stabilizer, isotonic agent, local anesthetic, etc. Examples of pH adjusting agents and buffers are sodium citrate, sodium acetate, sodium phosphate, etc. Examples of stabilizers are sodium pyrosulfite, EDTA, thioglycolic acid, thiolactic acid, etc. Examples of local anesthetics are procaine hydrochloride, lidocaine hydrochloride, etc.

Suppositories can be prepared in a usual manner by adding to the compound of the invention a pharmaceutically acceptable carrier already known in the art, such as polyethylene glycol, lanolin, cacao fat and oil, fatty acid triglyceride and, if desired, a surfactant, for example, tween (registered trademark).

Ointments can be prepared in a usual manner by blending to the compound of the invention a base, a stabilizer, a wetting agent, a preservative etc., which are generally used, and the resulting composition is admixed to give an ointment preparation. Examples of the base are liquid paraffin, white petrolatum, white beeswax, octyldodecyl alcohol, paraffin, etc. Examples of the preservative are methyl parahydroxybenzoate, ethyl parahydroxybenzoate, propyl parahydroxybenzoate, etc.

Plasters can be prepared in a usual manner by applying the ointments mentioned above, creams, gels, pastes, etc. to conventional supports. Examples of said supports are suitably woven fabrics and unwoven fabrics made of cotton, staple fiber or some other chemical fiber, films or foamed sheets made of plasticized polyvinyl chloride, polyethylene, polyurethane, etc.

The amount of the compound of the present invention to be incorporated into each of the dosage units varies with the symptoms of the patient or with the type of the preparations. The preferable amount per administration unit is about 1 to 1,000 mg for oral preparations, about 0.1 to 500 mg for injections, or about 5 to 1,000 mg for suppositries. The dosage per day of the drug in the above dosage form is variable with the symptoms, body weight, age, sex and other factors of the patient, but usually ranges from about 0.1 to 5,000 mg, preferably from about 1 to 1,000 mg for human adult. The preparation is preferably administered in a single dose or in two to four derided-doses.

EXAMPLES

The following examples dosage form examples and pharmacological test examples illustrate the present invention in further detail.

EXAMPLE 1

3,4-Bis(4-methoxyphenyl)isoxazole-5-acetic acid (1 g) was dissolved in 20 ml of dry tetrahydrofuran. Then, 43 mg of 4-dimethylaminopyridine, 905 mg of 1-ethyl-3-(3-dimethylaminopropyl)carbodiimide and 422 mg of 1,3-thiazolidine-2-thione were added. The resultant mixture was stirred at room temperature for 1 hour. Then, after addition of a solution of 386 mg of o-aminophenol in 10 ml of tetrahydrofuran, stirring was further continued for 24 hours. The reaction mixture was diluted with 80 ml of ethyl acetate, washed with saturated aqueous sodium hydrogen carbonate (30 ml×5 times), dried over anhydrous magnesium sulfate and concentrated under reduced pressure. The residue was purified by silica gel column chromatography (2% methanol-chloroform) to give 770 mg (yield 61%) of Compound 1 listed in Table 1.

The $^1$H-NMR data obtained for Compound 1 are shown below.

* Compound 1 $^1$H-NMR (DMSO-$d_6$) $\delta$:
3.76 (s, 6H), 3.99 (s, 2H), 6.91–7.82 (m, 12H), 9.54 (br.s, 1H), 9.87 (br.s, 1H)

EXAMPLES 2 AND 3

Compounds 2 and 3 specified in Table 1 were synthesized in the same manner as in Example 1.

The $^1$H-NMR data obtained for Compound 3 are shown below.

* Compound 3 $^1$H-NMR (DMSO-$d_6$) $\delta$: 3.76 (s, 6H), 3.99 (s, 2H), 6.91–7.38 (m, 9H), 7.71–8.35 (m, 3H), 10.84 (s, 1H)

EXAMPLE 4

Step A

To 430 ml of tert-butanol were added 128 g of deoxyanisoin, 67.3 g of potassium tert-butoxide and 116 g of methyl 3-methoxyacrylate. The mixture was stirred at 70° C. for 3 hours. After completion of the reaction, n-hexane was added to the reaction mixture, and the whole mixture was allowed to stand at room temperature. The resulting precipitate was collected by filtration and 1,000 ml of ethyl acetate and 300 ml of 3N sulfuric acid were added thereto for dissolution. The organic layer was separated, washed with 3N sulfuric acid and saturated aqueous sodium hydroxide solution in that order, and dried over anhydrous magnesium sulfate. The organic layer was then concentrated under reduced pressure to give 153 g (yield 90%) of methyl 4,5-bis(4-methoxyphenyl)-5-oxo-3-pentenoate as an oil.

Step B

A mixture of 24.5 g of methyl 4,5bis(4-methoxyphenyl)-5-oxo-3-pentenoate and 51.5 g of hydroxylamine hydrochloride in a mixture of 650 ml of methanol and 72 ml of water was heated under reflux for 3 hours. During this procedure, 0.9 equivalent of sodium hydrogen carbonate was added portionwise to the reaction mixture as the reaction progressed. After completion of the reaction, the methanol was distilled off under reduced pressure. Water and ethyl acetate were added to the residue for dissolution thereof, the organic layer was separated, washed with saturated aqueous sodium chloride solution and dried over anhydrous magnesium sulfate. The organic layer was then concentrated under reduced pressure and the residue was separated and purified by silica gel column chromatography (developing solvent: ethyl acetate:n-hexane=1:4) to give 23 g (yield 90%) of methyl 5-hydroxyimino-4,5-bis(4-methoxyphenyl)-3-pentenoate as an oil.

Step C

Methyl 5-hydroxyimino-4,5-bis(4-methoxyphenyl)-3-pentenoate (3.7 g) in 40 ml of acetic acid was stirred at 60° C. for 24 hours while blowing air into the mixture in the presence of 0.4 g of cobalt acetate. After completion of the reaction, 3N sulfuric acid was added and the resulting mixture was extracted with ethyl acetate. The organic layer was washed with saturated aqueous potassium carbonate solution and saturated aqueous sodium chloride solution in that order, and dried over anhydrous magnesium sulfate. The organic layer was then concentrated under reduced pressure and the residue was separated and purified by silica gel column chromatography (developing solvent: ethyl acetate:n-hexane=1:2) to give 3.3 g (yield 90%) of 5-methoxycarbonylmethyl-3,4-bis(4-methoxyphenyl)isoxazole.

Step D

Sodium borohydride (5.9 g) was added to a suspension of 5 g of 5-methoxycarbonylmethyl-3,4-bis(4-methoxyphenyl)isoxazole in 20 ml of methanol, and the resulting mixture was stirred for 1 hour with ice cooling. The reaction mixture was made acidic by portionwise addition of 1N hydrochloric acid and then extracted with 80 ml of ethyl acetate. The extract was washed with 20 ml of 1N hydrochloric acid and 20 ml of water in that order, then dried over anhydrous magnesium sulfate and concentrated under reduced pressure to give 4.5 g (yield 98%) of 5-(2-hydroxyethyl)-3,4-bis(4-methoxyphenyl)isoxazole.

Reaction formula (i)

4-Dimethylaminopyridine (60 mg) and 1.0 g of dicyclohexylcarbodiimide were added to a solution of 966 mg of 5-(2-hydroxyethyl)-3,4-bis(4-methoxyphenyl)isoxazole and 1.16 g of 3,4-bis(2-methoxyethoxymethoxy)cinnamic acid in 20 ml of dry methylene chloride, and the resulting mixture was stirred at room temperature for 3 hours. The crystalline precipitate was filtered off and washed with a small amount of methylene chloride. The mother liquor and the washings were combined and concentrated under reduced pressure. The residue was roughly purified by silica gel column chromatography (chloroform:methanol=10:1). The oily crude product obtained was dissolved in 40 ml of methanol, 300 mg of p-toluenesulfonic acid was added, and the mixture was stirred at room temperature for 15 hours. The reaction mixture was concentrated under reduced pressure and purified by silica gel column chromatography to give 1.1 g (yield 76%) of Compound 4 listed in Table 1.

EXAMPLE 5

Step E

Diethyl azodicarboxylate (0.62 ml) was added to a solution of 1.3 g of 5-(2-hydroxyethyl)-3,4-bis(4-methoxyphenyl)isoxazole (obtained in Example 4), 1.1 g of triphenylphosphine and 600 mg of phthalimide in 15 ml of tetrahydrofuran with ice cooling under a nitrogen atmosphere. The mixture was stirred for 20.5 hours. Diethyl ether (150 ml) was added to the reaction mixture for extraction. The extract was washed with 30 ml of water, dried over anhydrous magnesium sulfate, and concentrated under reduced pressure. The residue was purified by silica gel column chromatography (n=hexane:ethyl acetate=2:1) to give 1.5 g of the corresponding phthalimide compound.

Step F

This phthalimide compound (1.5 g) was suspended in 15 ml of ethanol, 165 mg of hydrazine hydrate was added, and the mixture was stirred at room temperature for 40.5 hours. The crystalline precipitate was filtered off and washed with 10 ml of ethanol. The mother liquor and the washings were combined and concentrated under reduced pressure. The residue was purified by silica gel column chromatography (20% methanol/chloroform) to give 600 mg (yield 46%) of 5-(2-aminoethyl)-3,4-bis(4-methoxyphenyl)isoxazole.

Reaction formula (ii)

To a solution of 600 mg of 5-(2-aminoethyl)-3,4-bis(4-methoxyphenyl)isoxazole and 334 mg of caffeic acid in 10 ml of N,N-dimethylformamide were added 300 mg of 1-hydroxybenzotriazole and 458 mg of dicyclohexylcarbodiimide. The mixture was stirred at room temperature for 2 hours. The crystalline precipitate was filtered off and washed with a small amount of N,N-dimethylformamide. The mother liquor and the washings were combined and concentrated under reduced pressure. The thus-obtained crude product was purified by silica gel column chromatography (20% methanol/chloroform) to give 880 mg (yield 69%) of Compound 5 listed in Table 1.

EXAMPLES 6 TO 14

Compounds 6 to 14 listed in Table 1 were synthesized in the same manner as in Examples 4 and 5.

The $^1$H-NMR data obtained for Compound 9 and Compounds 11 to 14 are shown below.

*Compound 9 $^1$H-NMR (CDCl$_3$) δ:
 3.03 (t, 2H), 3.70 (q, 2H), 3.78 (s, 6H), 3.90 (s, 3H), 5.92 (m, 1H), 6.00 (br., 1H), 6.18 (d, 1H), 6.80–7.40 (m, 11H), 7.48 (d, 1H)

* Compound 11 $^1$H-NMR (CDCl$_3$) δ:
 3.10 (t, 2H), 3.78 (q, 2H), 3.79 (s, 3H),13.81 (s, 3H), 3.94 (s, 3H), 5.90 (br., 1H), 6.32 (br., 1H), 6.80–7.40 (m, 11H)

* Compound 12 $^1$H-NMR (DMSO-d$_6$) δ:
 2.90 (t, 2H), 3.41 (q, 2H), 3.75 (s, 3H), 3.76 (s, 3H), 3.80 (s, 3H), 5.98 (d, 1H), 6.70–7.30 (m, 14H), 8.21 (t, 1H)

* Compound 13 $^1$H-NMR (DMSO-d$_6$) δ:
 2.98 (t, 2H), 3.50 (q, 2H), 3.83 (s, 3H), 3.85 (s, 3H), 3.90 (s, 6H), 6.08 (d, 1H), 6.86–7.40 (m, 13H), 8.34 (t, 1H), 8.74 (s, 1H)

* Compound 14 $^1$H-NMR (CDCl$_3$) δ:
 3.00 (t, 2H), 3.70 (q, 2H), 3.77 (s, 6H), 3.78 (s, 6H), 5.76 (d, 1H), 6.00 (t, 1H), 6.10 (s, 2H), 6.80–7.40 (m, 11H), 7.98 (s, 1H)

EXAMPLE 15

Deoxyanisoin ketoxime (10 g) was dissolved in 100 ml of tetrahydrofuran and, under a nitrogen atmosphere, 49 ml of 1.6M n-butyllithium was added dropwise at 10° C. or below. After an hour, a solution of 7.8 g of chloroacetic anhydride in 40 ml of tetrahydrofuran was added, and the mixture was stirred for 1.5 hours. To this solution was added 30 ml of concentrated sulfuric acid. Stirring was continued for 11.5 hours at room temperature. The reaction mixture was diluted with 200 ml of ethyl acetate, washed with three 50-ml portions of water, dried over anhydrous magnesium sulfate and concentrated under reduced pressure. The residue was purified by silica gel column chromatography (n-hexane:ethyl acetate=4:1) to give 3.8 g (yield 32%) of 5-chloromethyl-3,4-bis(4-methoxyphenyl)isoxazole.

5-Chloromethyl-3,4-bis(4-methoxyphenyl)isoxazole (1 g) was dissolved in 30 ml of methanol, and 30 ml of aqueous ammonia was added. The mixture was heated under reflux for 3 hours, then allowed to cool, and concentrated under reduced pressure. The residue was made acidic by addition of 4N hydrochloric acid/ethyl acetate and extracted with 100 ml of water. The aqueous layer was made alkaline by addition of potassium hydroxide and extracted twice with 100 ml of ethyl acetate. The organic layer was dried over anhydrous magnesium sulfate and then concentrated to dryness under reduced pressure. The thus-obtained 5-aminomethyl-3,4-bis(4-methoxyphenyl)isoxazole (450 mg) was dissolved in 10 ml of methylene chloride, then 450 mg of 5-(4'-$\beta$-methoxyethoxymethoxy-3'-methoxyphenyl)-2,4-pentanedienocarboxylic acid, 360 mg of dicyclohexyl carbodiimide and 50 mg of 4-dimethylaminopyridine were added, and the mixture was stirred at room temperature for 14 hours. The crystalline precipitate was filtered off, and the filtrate was concentrated under reduced pressure, and the residue was purified by silica gel column chromatography (0 to 0.5% methanol/chloroform). The thus-obtained residue was dissolved in 20 ml of methanol, 10 mg of p-toluenesulfonic acid was added, and the mixture was stirred at room temperature for 24 hours and then concentrated under reduced pressure. The residue was crystallized from ethanol to give 600 mg (yield 39%) of Compound 15 listed in Table 1.

EXAMPLE 16

Compound 16 listed in Table 1 was synthesized in the same manner as in Example 15.

The $^1$H-NMR data obtained for Compound 16 are shown below.

* Compound 16 $^1$H-NMR (CDCl$_3$) $\delta$:
3.80 (s, 3H), 3.83 (s, 3H), 3.93 (s, 6H), 4.68 (d, 2H), 5.66 (s, 1H), 5.88–5.95 (m, 2H), 6.69–7.43 (m, 13H)

EXAMPLE 17

Deoxyanisoin ketoxime (5 g) was dissolved in 50 ml of tetrahydrofuran and, under a nitrogen atmosphere, 28 ml of 1.6M n-butyllithium was added dropwise at 0° C. After 30 minutes, a solution of 2.4 g of glutaric anhydride in 20 ml of tetrahydrofuran was added dropwise, and the mixture was stirred at room temperature for 3 hours. The reaction mixture was made acidic with 1N hydrochloric acid and extracted with 100 ml of ethyl acetate. The ethyl acetate layer was extracted twice with 50 ml of 1N aqueous sodium hydroxide. The aqueous layer was made acidic with concentrated hydrochloric acid and extracted with 100 ml of ethyl acetate. This extract was dried over anhydrous magnesium sulfate and then concentrated under reduced pressure. The residue was dissolved in 80 ml of methanol, several drops of concentrated sulfuric acid was added, the mixture was stirred at room temperature for 12 hours and, then, the solvent was! distilled off under reduced pressure. The residue was dissolved in 100 ml of ethyl acetate, and the solution was washed with 50 ml of saturated aqueous sodium hydrogen carbonate solution and 50 ml of saturated aqueous sodium chloride solution, dried over anhydrous magnesium sulfate and concentrated under reduced pressure. The residue was purified by silica gel column chromatography (chloroform). A solution of 1.5 g of the oily compound obtained by the above-mentioned purification by silica gel column chromatography (chloroform) in 5 ml of tetrahydrofuran was added dropwise at −78° C. in a nitrogen atmosphere to a solution prepared by adding 2.8 ml of 1.6M n-butyllithium dropwise to a solution of 0.46 ml of dimethyl methylphosphonate in 15 ml of dry tetrahydrofuran and stirring the mixture for 30 minutes.

After stirring at −78° C. for 1 hour, the reaction mixture was poured into ice water and extracted with 80 ml of ethyl acetate. The extract was washed with 10 ml of 1N hydrochloric acid, 10 ml of water, 10 ml of saturated aqueous sodium hydrogen carbonate solution, 10 ml of water and 10 ml of saturated aqueous sodium chloride solution in that order, and dried over anhydrous magnesium sulfate. The ethyl acetate was distilled off under reduced pressure and the residue was purified by silica gel column chromatography (chloroform). A solution of 2.1 g of the residue obtained in 10 ml of tetrahydrofuran was added to a solution of 178 mg of sodium hydride in 16 ml of tetrahydrofuran at −15° C., the mixture was stirred at the same temperature for 30 minutes, then a solution of 1.0 g of 3,4-di(ethoxycarbonyloxy)benzaldehyde in 10 ml of tetrahydrofuran was added, and the resulting mixture was allowed to return to room temperature and then stirred for 4 hours. The reaction mixture was concent rated under reduced pressure and the residue was purified by silica gel column chromatography (chloroform:methanol=50:1) to give 2.6 (yield 20%) of Compound 17 listed in Table 1.

The $^1$H-NMR data obtained for Compound 17 are shown below.

* Compound 17 $^1$H-NMR (CDCl$_3$) $\delta$:
1.39 (t, 3H), 1.40 (t, 3H), 2.08 (m, 2H), 2.70 (t, 2H), 2.80 (t, 2H), 3.79 (s, 3H), 3.80 (s, 3H), 4.30 (q, 2H), 4.32 (q, 2H), 6.60 (d, 1H), 6.80–7.50 (m, 12H)

EXAMPLES 18 AND 19

Compounds 18 and 19 listed in Table 1 were synthesized in the same manner as in Example 17.

The $^1$H-NMR data obtained for Compounds 18 and 19 are shown below.

* Compound 18 $^1$H-NMR (CDCl$_3$) $\delta$:
1.40 (t, 3H), 2.10 (m, 2H), 2.22 (s, 6H), 2.70 (t, 2H), 2.82 (t, 2H), 3.79 (s, 3H), 3.80 (s, 3H), 4.32 (q, 2H), 6.60 (d, 1H), 6.80–7.42 (m, 11H)

* Compound 19 $^1$H-NMR (CDCl$_3$) $\delta$:
2.08 (m, 2H), 2.66 (t, 2H), 2.80 (t, 2H), 3.78 (s, 3H), 3.80 (s, 3H), 6.00 (s, 2H), 6.50 (d, 1H), 6.72–7.42 (m, 12H)

EXAMPLES 20 AND 21

Compounds 20 and 21 listed in Table 1 were synthesized in the same manner as in Example 17 except that succinic anhydride was used in lieu of glutaric anhydride.

The $^1$H-NMR data obtained for Compounds 20 and 21 are shown below.

* Compound 20 $^1$H-NMR (CDCl$_3$) $\delta$:
1.39 (t, 3H), 1.40 (t, 3H), 3.12 (s, 4H), 3.78 (s, 3H), 3.81 (s, 3H), 4.35 (q, 2H), 4.36 (q, 2H), 6.68 (d, 1H), 6.79–7.50 (m, 12H)

* Compound 21 $^1$H-NMR (CDCl$_3$) $\delta$:
1.40 (t, 3H), 3.12 (s, 4H), 3.79 (s, 3H), 3.82 (s, 3H), 3.90 (s, 3H), 4.32 (q, 2H), 6.66 (d, 1H), 6.80–7.52 (m, 12H)

EXAMPLE 22

A 450 mg portion of Compound 5 obtained in Example 5 was dissolved in 10 ml of pyridine, 0.2 ml of ethyl chlorocarbonate was added with ice cooling and the mixture was stirred for 10 minutes. After addition of ice, the reaction mixture was extracted with 80 ml of methylene chloride, and the organic layer was washed with 20 ml of water, dried over anhydrous magnesium sulfate and concentrated under reduced pressure. The residue was purified by silica gel column chromatography (chloroform) to give 560 mg (yield 96%) of Compound 22 listed in Table 1.

The $^1$H-NMR data obtained for Compound 22 are shown below.

*Compound 22 $^1$H-NMR (CDCl$_3$) δ:
1.38 (t, 6H), 3.06 (m, 2H), 3.69–3.74 (m, 2H), 3.77 (s, 3H), 3.79 (s, 3H), 4.33 (dd, 4H), 6.00 (m, 1H), 6.20 (d, 1H), 6.81–7.53 (m, 12H)

EXAMPLES 23 TO 33

Compounds 23 to 33 listed in Table 1 were synthesized in the same manner as in Example 22.

The $^1$H-NMR data obtained for Compounds 23 to 25 and Compounds 27 to 33 are shown below.

* Compound 23 $^1$H-NMR (CDCl$_3$) δ:
1.40 (t, 3H), 3.08 (t, 2H), 3.72 (q, 2H), 3.78 (s, 3H), 3.79 (s, 3H), 3.90 (s, 3H), 4.28 (q, 2H), 6.01 (t, 1H), 6.22 (d, 1H), 6.79–7.60 (m, 12H)

* Compound 24 $^1$H-NMR (CDCl$_3$) δ:
1.34 (t, 3H), 3.06 (m, 2H), 3.74 (m, 2H), 3.79 (s, 3H), 3.80 (s, 3H), 3.88 (s, 6H), 4.32 (dd, 2H), 5.94 (m, 1H), 6.25 (d, 1H), 6.73 (s, 2H), 6.85–7.39 (m, 8H), 7.50 (d, 1H)

* Compound 25 $^1$H-NMR (CDCl$_3$) δ:
1.38 (t, 3H), 3.02 (t, 2H), 3.68 (q, 2H), 3.78 (s, 3H), 3.81 (s, 3H), 3.88 (s, 3H), 4.28 (q, 2H), 5.90 (d, 1H), 6.00 (t, 1H), 6.68–7.40 (m, 14H)

*Compound 27 $^1$H-NMR (CDCl$_3$) δ:
1.40 (t, 3H), 3.00 (t, 2H), 3.70 (q, 2H), 3.79 (s, 3H), 3.81 (s, 3H), 3.86 (s, 6H), 4.30 (q, 2H), 5.78 (t, 1H), 5.80 (d, 1H), 6.42 (s, 2H), 6.78–7.40 (m, 11H)

* Compound 28 $^1$H-NMR (CDCl$_3$) δ:
1.55 (t, 3H), 3.80 (s, 3H), 3.83 (s, 3H), 3.89 (s, 3H), 4.32 (dd, 2H), 5.92–5.97 (m, 2H), 6.68 (d, 2H), 6.72–7.42 (m, 14H)

* Compound 29 $^1$H-NMR (CDCl$_3$) δ:
1.39 (t, 3H), 3.80 (s, 3H), 3.83 (s, 3H), 3.88 (s, 6H), 4.32 (dd, 2H), 4.68 (d, 2H), 5.95 (d, 1H), 6.03 (m, 1H), 6.68–7.42 (m, 13H)

* Compound 30 $^1$H-NMR (DMSO-d$_6$) δ:
2.89 (t, 3H), 3.42 (q, 2H), 3.69 (s, 3H), 3.73 (s, 3H), 3.75 (s, 3H), 3.80 (s, 6H), 4.50 (s, 2H), 6.08 (d, 1H), 6.80–7.30 (m, 12H), 8.31 (t, 1H)

* Compound 31 $^1$H-NMR (CDCl$_3$) δ:
0.90 (t, 3H), 1.24–1.50 (m, 6H), 1.74 (t, 2H), 3.00 (t, 2H), 3.70 (q, 2H), 3.79 (s, 3H), 3.81 (s, 3H), 3.88 (s, 6H), 4.24 (t, 2H), 5.88 (d, 1H), 6.00 (t, 1H), 6.68–7.40 (m, 13H)

*Compound 32 $^1$H-NMR (CDCl$_3$) δ:
0.98 (s, 3H), 1.01 (s, 3H), 1.99–2.01 (m, 1H), 3.04 (m, 2H), 3.68–3.75 (m, 2H), 3.80 (s, 3H), 3.82 (s, 3H), 3.87 (s, 6H), 4.05 (d, 2H), 5.86–5.91 (m, 2H), 6.69–7.40 (m, 13H)

*Compound 33 $^1$H-NMR (CDCl$_3$) δ:
2.34 (s, 3H), 3.04 (m, 2H), 3.68–3.75 (m, 2H), 3.80 (s, 3H), 3.82 (s, 3H), 3.86 (s, 6H), 5.83–5.91 (m, 2H), 6.68–7.40 (m, 13H)

EXAMPLE 34

A 300 mg portion of Compound 13 obtained in Example 13 was dissolved in 5 ml of methylene chloride, 94 mg of N-tert-butoxycarbonylglycine and 78 mg of 4-dimethylaminopyridine were added and then, with ice cooling, 132 mg of N,N'-dicyclohexylcarbodiimide was added and the mixture was stirred for 2 days. The crystalline precipitate was filtered off and washed with ethyl acetate. The mother liquor and the washings were combined, diluted with 70 ml of ethyl acetate, washed with 15 ml of water, dried over anhydrous magnesium sulfate and concentrated under reduced pressure. The residue was purified by silica gel column chromatography (chloroform:methanol=15:1). The thus-obtained oily substance was dissolved in 5 ml of ethyl acetate, 20 ml of 4N hydrochloric acid in ethyl acetate was added to the solution with ice cooling and the resulting mixture was stirred for 1 hour. The crystalline precipitate was collected by filtration, washed with a small amount of ether and dried under-reduced pressure to give 277 mg (yield 80%) of Compound 34 listed in Table 1.

EXAMPLES 35 TO 37

Compounds 35 to 37 listed in Table 1 were synthesized in the same manner as in Example 34.

The $^1$H-NMR data obtained for Compounds 36 and 37 are shown below.

* Compound 36 $^1$H-NMR (CDCl$_3$) δ:
3.00–3.04 (m, 2H), 3.06 (s, 6H), 3.67–3.70 (m, 2H), 3.79 (s, 3H), 3.81 (s, 3H), 3.81 (s, 6H), 5.82 (d, 1H), 6.12 (m, 1H), 6.58–7.38 (m, 15H), 8.06–8.10 (m, 2H)

* Compound 37 $^1$H-NMR (CDCl$_3$) δ:
3.04 (m, 2H), 3.68–3.75 (m, 2H), 3.79 (s, 3H), 3.82 (s, 3H), 3.85 (s, 6H), 5.92 (d, 1H), 6.04 (m, 1H), 6.73–7.48 (m, 14H), 8.45–8.49 (m, 1H), 8.84–8.85 (m, 1H), 9.42 (s, 1H)

EXAMPLE 38

A 800 mg portion of Compound 17 obtained in Example 17 was dissolved in a mixture of methanol, tetrahydrofuran and water (4:3:1), 250 mg of sodium hydroxide was added, and the mixture was stirred at room temperature for 4 hours. The reaction mixture was concentrated under reduced pressure, 30 ml of water was added, and the mixture was made acidic (pH=5.0) with concentrated hydrochloric acid and extracted with 100 ml of ethyl acetate. The ethyl acetate layer was dried over anhydrous magnesium sulfate and concentrated under reduced pressure, and the residue was purified by silica gel column chromatography (chloroform:methanol=15:1) to give 487 mg (yield 82%) of Compound 38 listed in Table 1.

EXAMPLES 39 TO 42

Compounds 39 to 42 listed in Table 1 were synthesized in the same manner as in Example 38.

* Compound 39 $^1$H-NMR (CDCl$_3$) δ:
2.04–2.15 (m, 2H), 2.70–2.75 (m, 2H), 2.81–2.87 (m, 2H), 3.80 (s, 3H), 3.81 (s, 3H), 3.93 (s, 6H), 5.81 (s, 1H), 6.55 (d, 1H), 6.79–7.45 (m, 11H)

* Compound 40 $^1$H-NMR (CDCl$_3$) δ:
2.09 (m, 3H), 2.26 (s, 6H), 2.69 (m, 2H), 2.83 (m, 2H), 3.80 (s, 3H), 3.80 (s, 3H), 5.08 (s, 1H), 6.54 (d, 1H), 6.80–7.43 (m, 11H)

* Compound 41 $^1$H-NMR (CDCl$_3$) δ:
3.10 (s, 4H), 3.79 (s, 3H), 3.82 (s, 3H), 3.92 (s, 3H), 5.90 (s, 1H), 6.60 (d, 1H), 6.80–7.52 (m, 12H)

EXAMPLES 43 AND 44

Using Compound 38 obtained in Example 38, Compounds 43 and 44 listed in Table 1 were synthesized in the same manner as in Example 22.

The $^1$H-NMR data obtained for Compounds 43 and 44 are shown below.

* Compound 43 $^1$H-NMR (CDCl$_3$) δ:
2.08 (q, 2H), 2.29 (s, 3H), 2.30 (s, 3H), 2.69 (t, 2H), 2.82 (t, 2H), 3.77 (s, 3H), 3.78 (s, 3H), 6.58 (d, 1H), 6.80–7.42 (m, 12H)

* Compound 44 $^1$H-NMR (CDCl$_3$) δ:
1.38 (t, 12H), 2.08 (q, 2H), 2.70 (t, 2H), 2.84 (t, 2H), 3.79 (s, 3H), 3.80 (s, 3H), 4.28 (q, 8H), 6.60 (d, 1H), 6.80–7.60 (m, 12H)

EXAMPLE 45

To a solution of 5 g of deoxyanisoin ketoxime in 90 ml of tetrahydrofuran was added dropwise 29 ml of 1.6M n-butyllithium at 10° C. or below under a nitrogen atmosphere. After an hour, a solution of 5.9 g of 1,3-dioxolane-2-methyl-ethyl ester in 20 ml of tetrahydrofuran was added, and the mixture was stirred for 2 hours. Then, 20 ml of concentrated sulfuric acid was added and the mixture was stirred at room temperature for 20 hours. The reaction mixture was diluted with 200 ml of ethyl acetate, washed with water, dried over anhydrous magnesium sulfate and concentrated under reduced pressure. The residue was purified by silica gel column chromatography (n-hexane:ethyl acetate=4:1) to give 820 mg (yield 14%) of 5-acetyl-3,4-bis(4-methoxyphenyl)isoxazole.

A 800 mg portion of this product was suspended in 20 ml of ethanol, 376 mg of vanillin and 1 ml of piperidine were added, and the mixture was heated under reflux for 7 hours. The mixture was allowed to cool and then concentrated under reduced pressure and the residue was purified by silica gel column chromatography (n-hexane:ethyl acetate=1:1) to give 290 mg (yield 26%) of Compound 45 listed in Table 1.

EXAMPLE 46

Compound 46 listed in Table 1 was synthesized in the same manner as in Example 45.

EXAMPLE 47

3,4-Bis(4-methoxyphenyl)isoxazole-5-acetic acid (2 g), 896 mg of vanillin and 602 mg of piperidine were warmed at 40° C. for 3 hours to give a molten mixture and then extracted with 120 ml of ethyl acetate. The extract was washed with water, dried over anhydrous magnesium sulfate and concentrated under reduced pressure. The residue was purified by silica gel column chromatography (chloroform) and recrystallized from ethanol to give 1.9 g (yield 75%) of Compound 47 listed in Table 1.

EXAMPLE 48

A 530 mg portion of Compound 23 obtained in Example 23 was dissolved in 20 ml of benzene, 396 mg of Lawesson's reagent was added, and the mixture was stirred at 60° C. for 2 hours. The mixture was allowed to cool and then concentrated under reduced pressure. The residue was purified by silica gel column chromatography (n-hexane:ethyl acetate=2 to 1:1). The thus-obtained residue was dissolved in tetrahydrofuran-methanol-water (10 ml:10 ml:5 ml), 43 mg of potassium hydroxide was added, and the mixture was stirred at room temperature for 30 minutes. The mixture was made acidic by addition of saturated aqueous ammonium chloride solution and extracted with 50 ml of ethyl acetate. The extract was dried over anhydrous magnesium sulfate and concentrated to dryness under reduced pressure. The residue was crystallized from ethanol to give 256 mg (yield 54%) of Compound 48 listed in Table 1.

The structure, melting point, molecular formula and elemental analysis data for each of the compounds of the present invention as obtained above in Example 1 to 48 are shown in Table 1. In the elemental analysis column, the upper row values for each compound are found values and the lower row values are theoretical values.

TABLE 1

| No. | Structure | M.P. (°C.) | Chemical Formula | Elemental Analysis C | H | N |
|-----|-----------|------------|------------------|---|---|---|
| 1 | 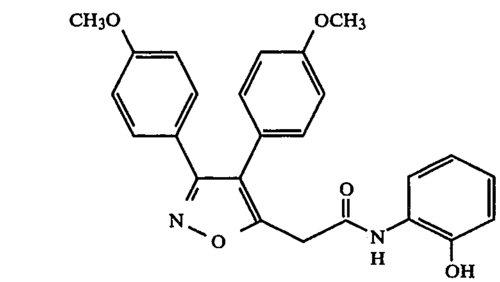 | amorphous | $C_{25}H_{22}N_2O_5$ | 69.57 69.76 | 5.62 5.15 | 6.20 6.51 |
| 2 | 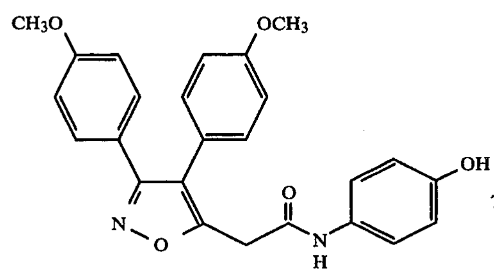 | 124~125 | $C_{25}H_{22}N_2O_5 \cdot 7/10H_2O$ | 67.92 67.77 | 5.63 5.32 | 5.81 6.32 |
| 3 | 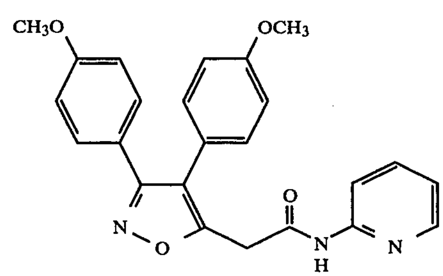 | amorphous | $C_{24}H_{21}N_3O_4$ | 69.02 69.39 | 5.25 5.10 | 9.87 10.11 |

TABLE 1-continued

| No. | Structure | M.P. (°C.) | Chemical Formula | Elemental Analysis C | H | N |
|---|---|---|---|---|---|---|
| 4 | 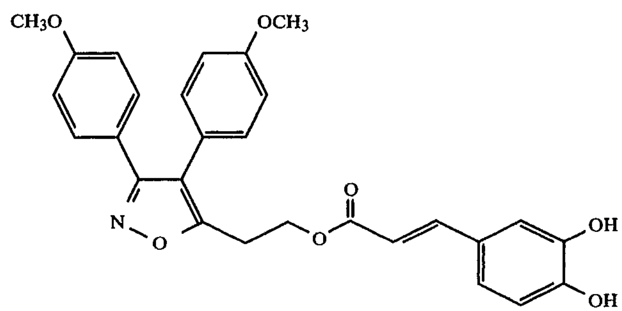 | 187~188 | C<sub>28</sub>H<sub>25</sub>NO<sub>7</sub> | 68.73 68.98 | 5.32 5.17 | 2.86 2.87 |
| 5 | 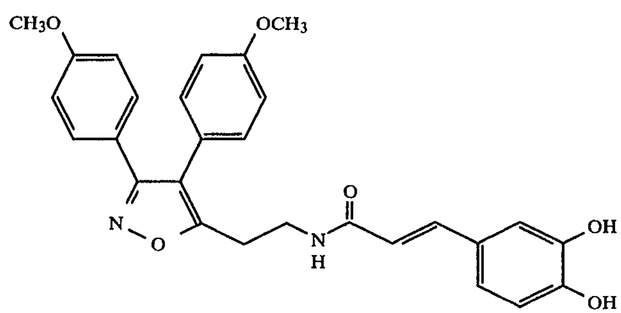 | 214~215 | C<sub>28</sub>H<sub>26</sub>N<sub>2</sub>O<sub>6</sub> | 68.92 69.12 | 5.47 5.39 | 5.71 5.76 |
| 6 | 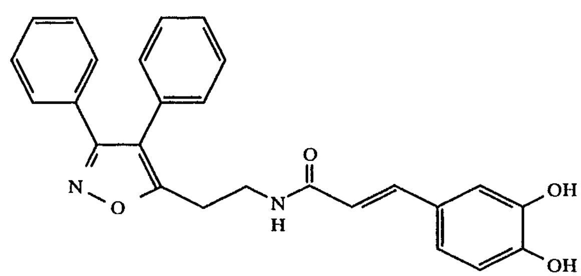 | 217~218.5 | C<sub>26</sub>H<sub>22</sub>N<sub>2</sub>O<sub>4</sub> | 72.93 73.22 | 5.59 5.20 | 6.49 6.57 |

TABLE 1-continued

| No. | Structure | M.P. (°C.) | Chemical Formula | Elemental Analysis C | H | N |
|---|---|---|---|---|---|---|
| 7 | 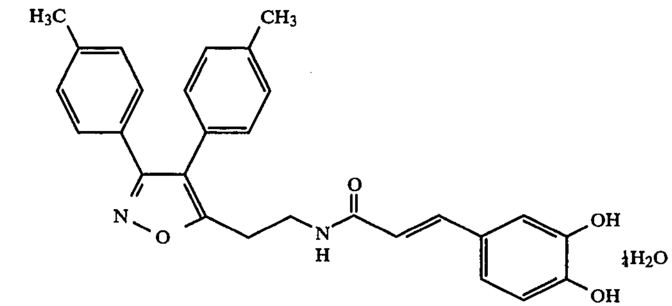 | 230~231 | $C_{28}H_{26}N_2O_4 \cdot \frac{1}{2} H_2O$ | 73.42<br>73.26 | 6.09<br>5.81 | 6.05<br>6.10 |
| 8 | 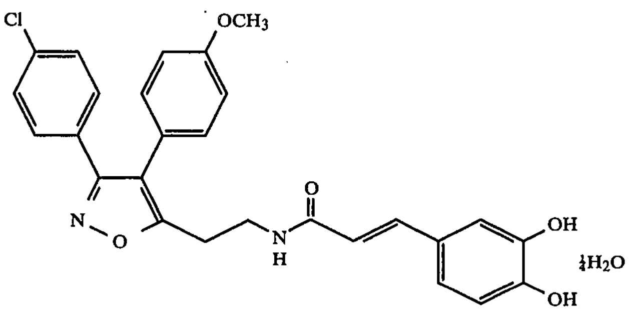 | 212.5~214 | $C_{27}H_{23}N_2O_5Cl \cdot \frac{1}{2} H_2O$ | 65.64<br>65.45 | 5.06<br>4.78 | 5.58<br>5.65 |
| 9 | 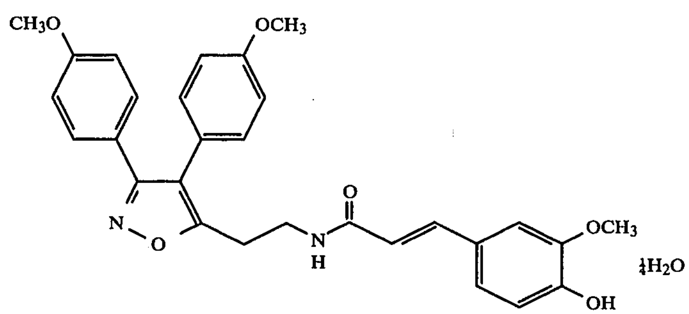 | amorphous | $C_{29}H_{28}N_2O_6 \cdot \frac{1}{2} H_2O$ | 68.96<br>69.01 | 5.63<br>5.60 | 5.54<br>5.53 |

TABLE 1-continued

| No. | Structure | M.P. (°C.) | Chemical Formula | Elemental Analysis C H N |
|---|---|---|---|---|
| 10 | 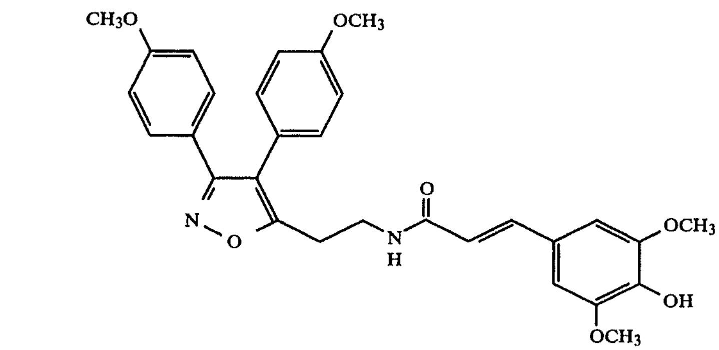 | 188~189 | $C_{30}H_{30}N_2O_7$ | 67.91 5.83 5.15<br>67.91 5.70 5.28 |
| 11 | 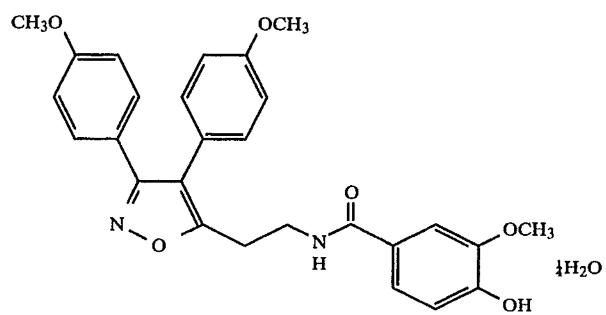 | | $C_{27}H_{26}N_2O_6 \cdot \frac{1}{4} H_2O$ | 67.73 5.58 5.61<br>67.69 5.52 5.84 |
| 12 | 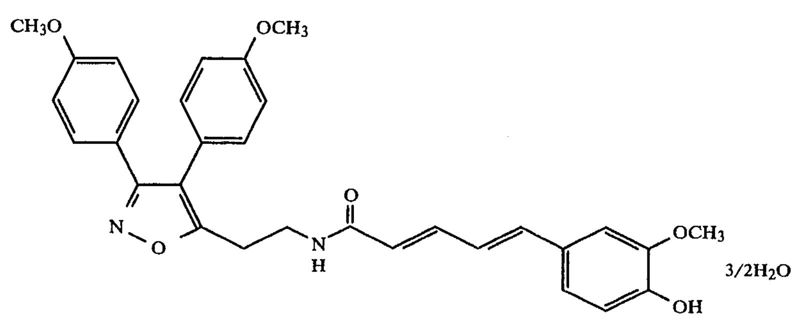 | | $C_{31}H_{30}N_2O_6 \cdot 3/2\, H_2O$ | 67.22 5.79 5.50<br>67.25 5.73 5.06 |

TABLE 1-continued

| No. | Structure | M.P. (°C.) | Chemical Formula | Elemental Analysis C H N |
|---|---|---|---|---|
| 13 | 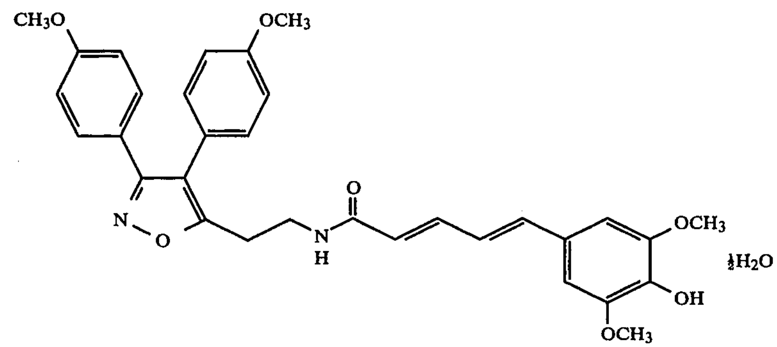 | amorphous | $C_{32}H_{32}N_2O_7 \cdot \frac{1}{2} H_2O$ | 67.63 6.01 4.72<br>67.95 5.88 4.95 |
| 14 | 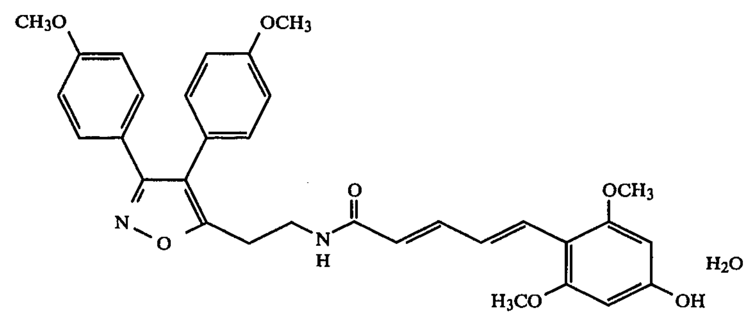 | amorphous | $C_{32}H_{32}N_2O_7 \cdot H_2O$ | 67.02 5.73 4.88<br>66.88 5.96 4.87 |
| 15 | 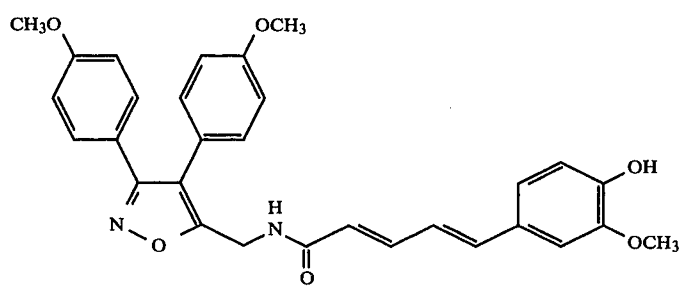 | 174~175 | $C_{30}H_{28}N_2O_6$ | 70.19 5.51 5.43<br>70.30 5.51 5.47 |

TABLE 1-continued

| No. | Structure | M.P. (°C.) | Chemical Formula | Elemental Analysis C | H | N |
|---|---|---|---|---|---|---|
| 16 | 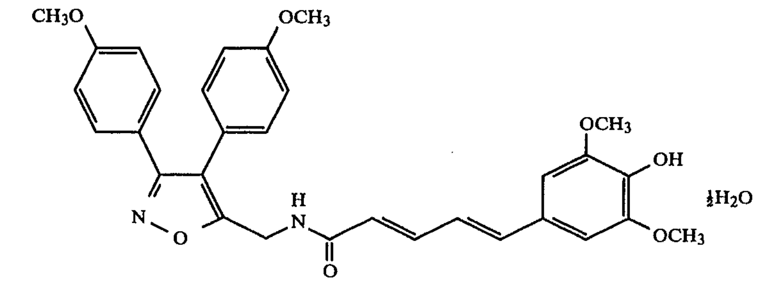 | amorphous | $C_{31}H_{30}N_2O_7 \cdot \frac{1}{2} H_2O$ | 67.63<br>67.50 | 5.90<br>5.66 | 4.74<br>5.08 |
| 17 | 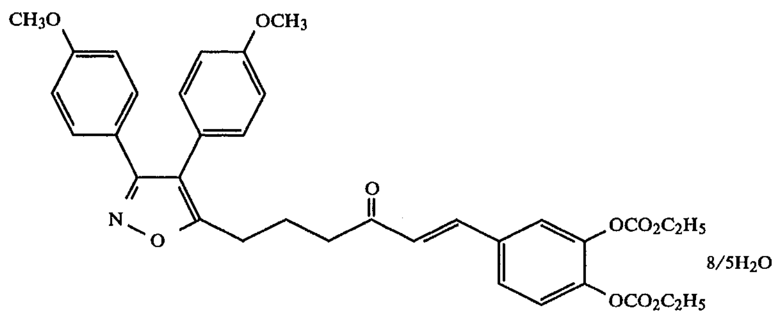 | amorphous | $C_{35}H_{35}NO_{10} \cdot 8/5 H_2O$ | 63.78<br>63.83 | 5.48<br>5.52 | 2.05<br>2.12 |
| 18 | 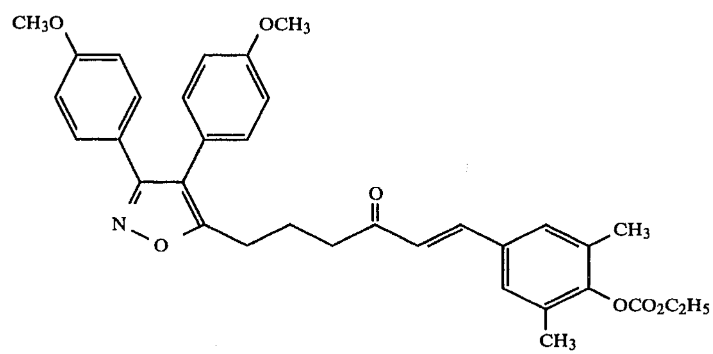 | amorphous | $C_{34}H_{35}NO_7$ | 71.65<br>71.68 | 6.29<br>6.19 | 2.53<br>2.45 |

TABLE 1-continued

| No. | Structure | M.P. (°C.) | Chemical Formula | Elemental Analysis C | H | N |
|---|---|---|---|---|---|---|
| 19 | (structure) | amorphous | $C_{30}H_{27}NO_6$ | 72.56 / 72.41 | 5.54 / 5.47 | 2.81 / 2.81 |
| 20 | (structure) | amorphous | $C_{34}H_{33}NO_{10}$ | 66.29 / 66.33 | 5.42 / 5.42 | 2.24 / 2.27 |
| 21 | (structure) | amorphous | $C_{32}H_{31}NO_8$ | 68.95 / 68.92 | 5.68 / 5.60 | 2.55 / 2.51 |

TABLE 1-continued

| No. | Structure | M.P. (°C.) | Chemical Formula | Elemental Analysis C H N |
|---|---|---|---|---|
| 22 | 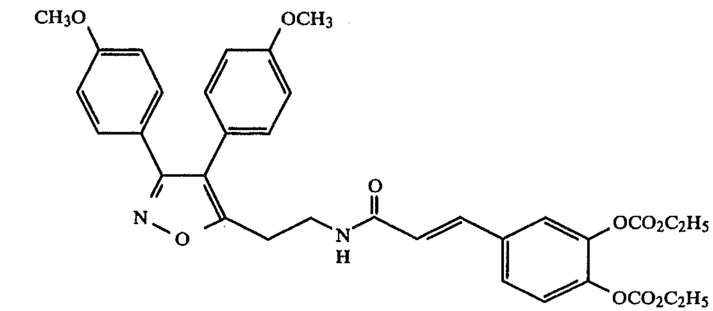 | amorphous | $C_{34}H_{34}N_2O_{10}$ | 64.71 5.67 4.45<br>64.75 5.43 4.44 |
| 23 | 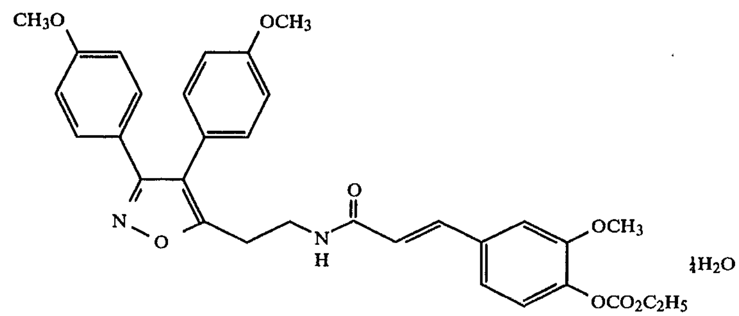 | amorphous | $C_{32}H_{32}N_2O_8 \cdot \frac{1}{2} H_2O$ | 66.54 5.47 4.87<br>66.59 5.63 4.85 |
| 24 | 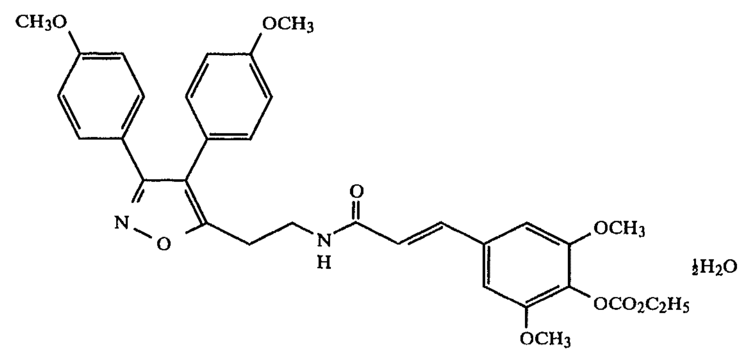 | amorphous | $C_{33}H_{34}N_2O_9 \cdot \frac{1}{2} H_2O$ | 64.89 5.86 4.37<br>64.80 5.77 4.58 |

TABLE 1-continued

| No. | Structure | M.P. (°C.) | Chemical Formula | Elemental Analysis C | H | N |
|---|---|---|---|---|---|---|
| 25 | 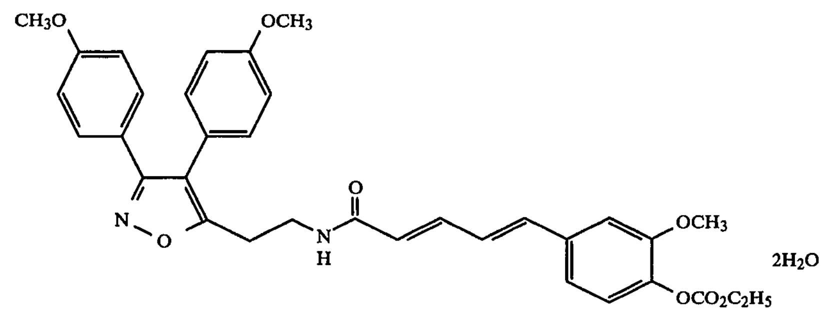 | amorphous | $C_{34}H_{35}N_2O_8 \cdot 2H_2O$ | 66.54<br>66.59 | 5.47<br>5.63 | 4.87<br>4.85 |
| 26 | 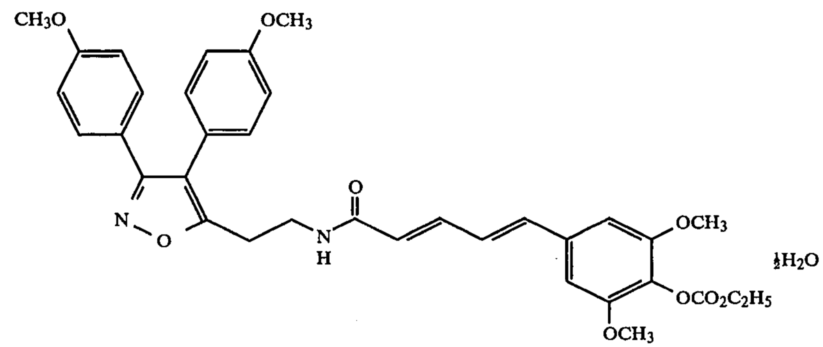 | 165~167 | $C_{35}H_{36}N_2O_9 \cdot \frac{1}{2}H_2O$ | 65.71<br>65.92 | 5.92<br>5.84 | 4.16<br>4.39 |
| 27 | 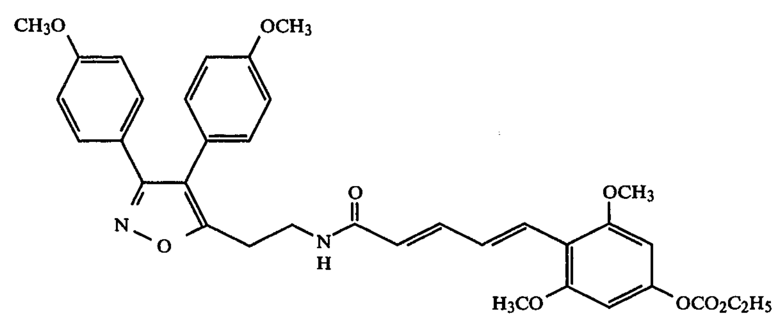 | amorphous | $C_{35}H_{36}N_2O_9$ | 66.83<br>66.86 | 5.77<br>5.77 | 4.51<br>4.45 |

TABLE 1-continued

| No. | Structure | M.P. (°C) | Chemical Formula | Elemental Analysis C H N |
|---|---|---|---|---|
| 28 | 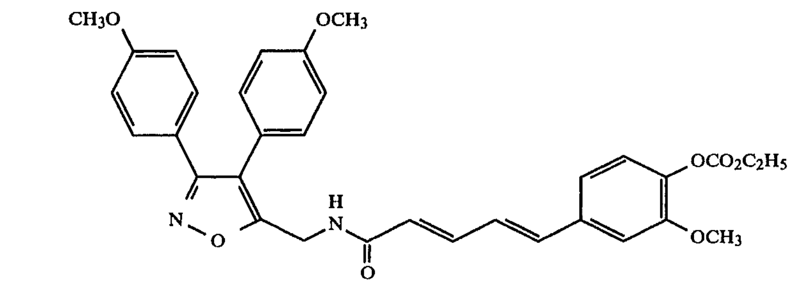 | amorphous | $C_{33}H_{32}N_2O_8$ | 67.31 5.70 4.80 / 67.28 5.56 4.76 |
| 29 | 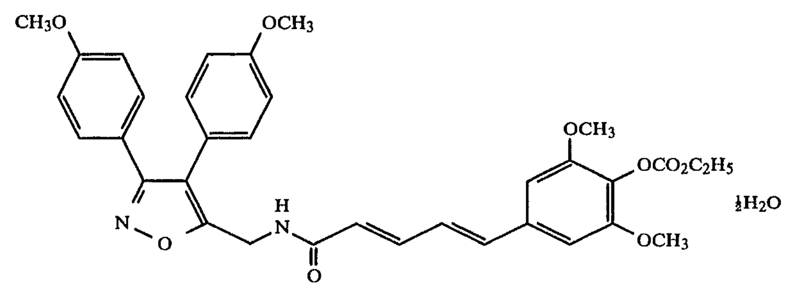 | amorphous | $C_{34}H_{34}N_2O_9 \cdot \frac{1}{2}H_2O$ | 65.32 5.96 4.53 / 65.48 5.67 4.49 |
| 30 | 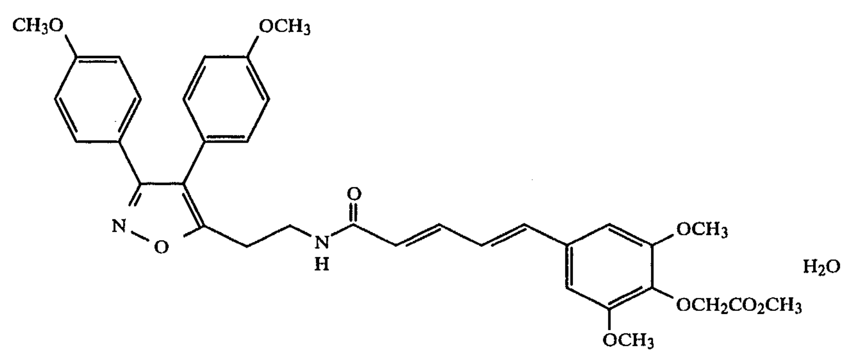 | amorphous | $C_{35}H_{36}N_2O_9 \cdot H_2O$ | 65.23 5.85 4.28 / 65.00 5.92 4.33 |

TABLE 1-continued

| No. | Structure | M.P. (°C.) | Chemical Formula | Elemental Analysis C | H | N |
|---|---|---|---|---|---|---|
| 31 | (structure shown) | amorphous | $C_{39}H_{44}N_2O_9 \cdot H_2O$ | 68.20<br>68.20 | 6.67<br>6.75 | 4.06<br>4.07 |
| 32 | (structure shown) | amorphous | $C_{37}H_{40}N_2O_9$ | 67.47<br>67.66 | 6.31<br>6.13 | 4.28<br>4.27 |
| 33 | (structure shown) | amorphous | $C_{34}H_{34}N_2O_8$ | 67.80<br>68.21 | 5.81<br>5.72 | 4.56<br>4.68 |

TABLE 1-continued

| No. | Structure | M.P. (°C.) | Chemical Formula | Elemental Analysis C H N |
|---|---|---|---|---|
| 34 | 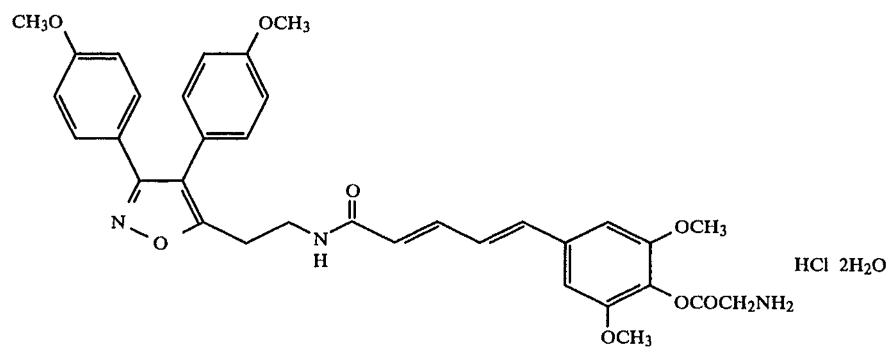 | 133~135 | $C_{34}H_{35}N_3O_8 \cdot HCl \cdot 2H_2O$ | 59.68 5.58 5.91<br>59.51 5.87 6.12 |
| 35 | 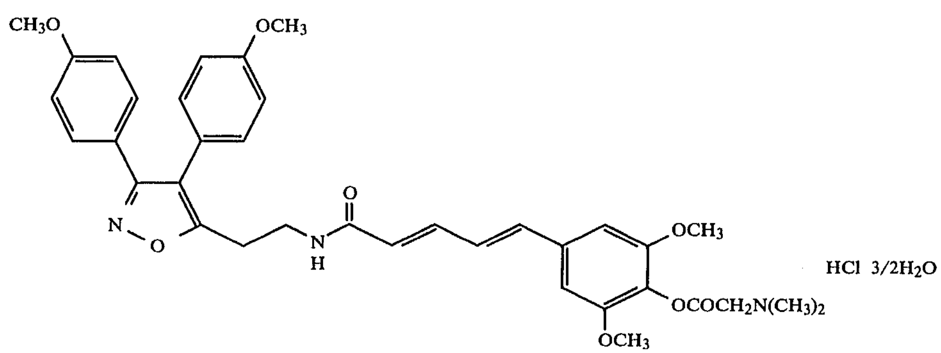 | 145~148 | $C_{36}H_{39}N_3O_8 \cdot HCl \cdot \frac{3}{2}H_2O$ | 61.24 6.00 5.87<br>61.39 6.15 5.96 |

TABLE 1-continued

| No. | Structure | M.P. (°C.) | Chemical Formula | Elemental Analysis C H N |
|---|---|---|---|---|
| 36 | 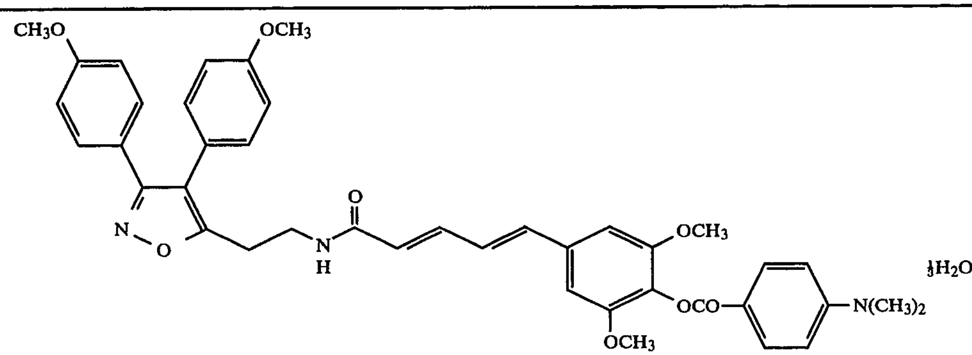 | amorphous | $C_{41}H_{41}N_3O_8 \cdot \frac{1}{2}H_2O$ | 69.44 6.06 5.76<br>69.77 5.86 5.92 |
| 37 | 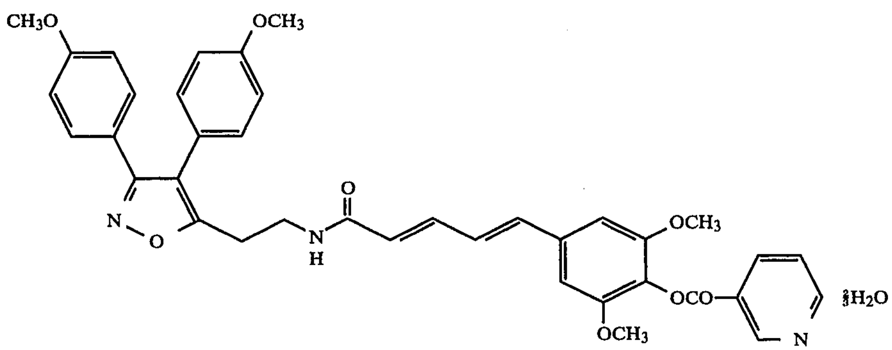 | amorphous | $C_{38}H_{35}N_3O_8 \cdot \frac{3}{2}H_2O$ | 67.50 5.42 6.33<br>67.74 5.46 6.23 |
| 38 | 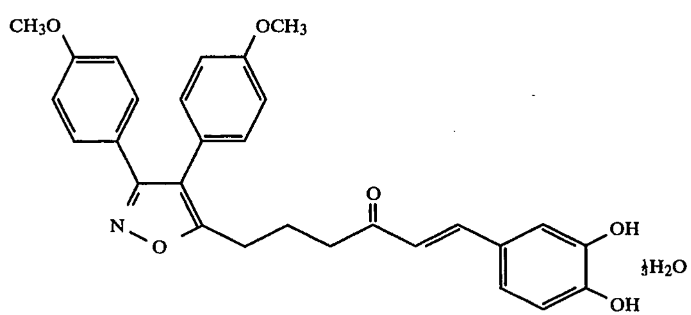 | 78~81 | $C_{29}H_{27}NO_6 \cdot \frac{1}{2}H_2O$ | 70.41 5.94 2.80<br>70.86 5.59 2.84 |

TABLE 1-continued

| No. | Structure | M.P. (°C.) | Chemical Formula | Elemental Analysis C | H | N |
|---|---|---|---|---|---|---|
| 39 | 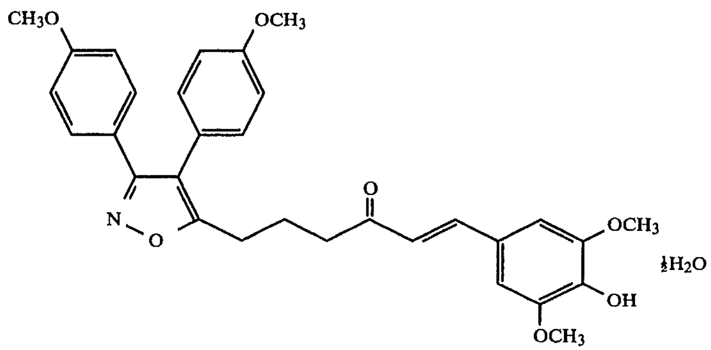 | amorphous | $C_{31}H_{31}NO_7 \cdot \frac{1}{2} H_2O$ | 69.28<br>69.12 | 5.86<br>5.98 | 2.61<br>2.60 |
| 40 | 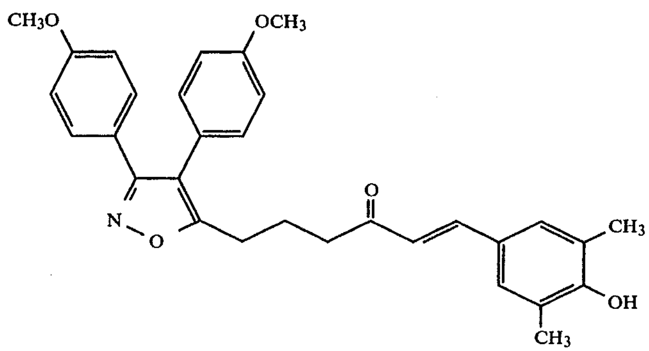 | amorphous | $C_{31}H_{31}NO_5$ | 74.36<br>74.82 | 6.36<br>6.28 | 2.81<br>2.81 |
| 41 | 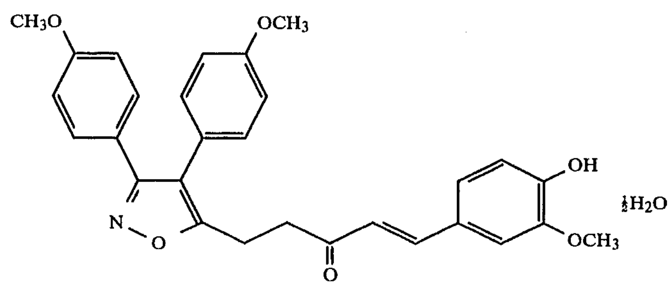 | amorphous | $C_{29}H_{27}NO_6 \cdot \frac{1}{2} H_2O$ | 70.69<br>70.43 | 5.81<br>5.70 | 2.82<br>2.83 |

TABLE 1-continued

| No. | Structure | M.P. (°C.) | Chemical Formula | Elemental Analysis C | H | N |
|---|---|---|---|---|---|---|
| 42 | (4-methoxyphenyl)-isoxazole with pentadienamide linked to 3,5-dimethoxy-4-(OCH₂CO₂H) phenyl · 3/2 H₂O | 106~110 | $C_{34}H_{34}N_2O_9 \cdot 3/2\, H_2O$ | 63.55  63.63 | 5.53  5.81 | 4.32  4.36 |
| 43 | bis(4-methoxyphenyl)-isoxazole linked via ketone chain to 3,4-bis(OCOCH₃)phenyl | amorphous | $C_{33}H_{31}NO_8$ | 69.51  69.58 | 5.54  5.48 | 2.49  2.49 |
| 44 | bis(4-methoxyphenyl)-isoxazole linked via ketone chain to 3,4-bis(OPO(OC₂H₅)₂)phenyl | amorphous | $C_{34}H_{45}NO_{12}P_2$ | 58.17  58.65 | 6.15  5.98 | 1.85  1.84 |

TABLE 1-continued

| No. | Structure | M.P. (°C.) | Chemical Formula | Elemental Analysis C | H | N |
|---|---|---|---|---|---|---|
| 45 | 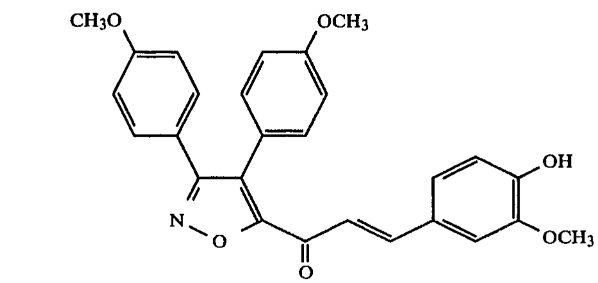 | 168~170 | $C_{27}H_{23}NO_6$ | 70.88<br>70.89 | 5.37<br>5.07 | 2.89<br>3.06 |
| 46 | 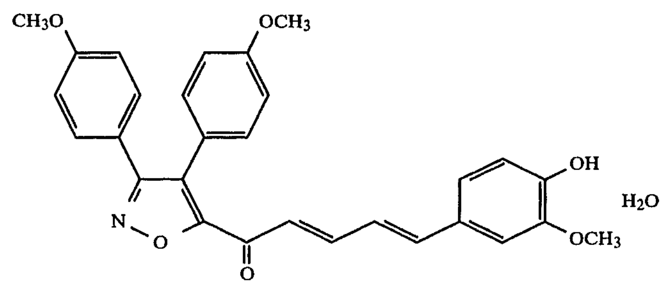 | 160~162 | $C_{29}H_{25}NO_6 \cdot H_2O$ | 69.68<br>69.45 | 5.54<br>5.43 | 2.73<br>2.79 |
| 47 | 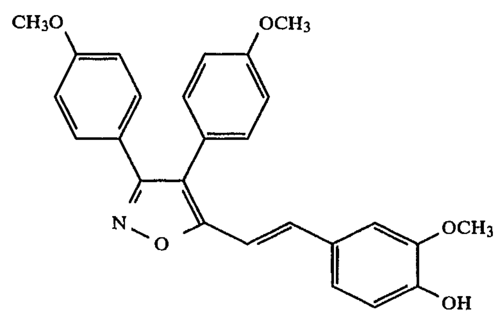 | 141~142 | $C_{26}H_{23}NO_5$ | 72.48<br>71.71 | 5.60<br>5.40 | 3.18<br>3.26 |

TABLE 1-continued
| No. | Structure | M.P. (°C.) | Chemical Formula | Elemental Analysis C H N |
|---|---|---|---|---|
| 48 | 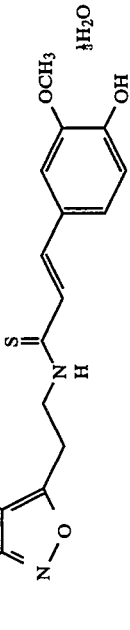 | 141~142 | $C_{29}H_{28}N_2O_5S \cdot \frac{1}{2} H_2O$ | 66.76 5.91 4.91<br>66.65 5.53 5.36 |

DOSAGE FORM EXAMPLES

Several dosage form examples in which certain compounds of the invention are used are give below.

DOSAGE FORM EXAMPLE 1

Tablets

Tablets were prepared in the conventional manner according to the following formulation.

| | |
|---|---|
| Compound 1 | 100 mg |
| Lactose | 47 mg |
| Corn starch | 50 mg |
| Crystalline cellulose | 50 mg |
| Hydroxypropylcellulose | 15 mg |
| Talc | 2 mg |
| Magnesium stearate | 2 mg |
| Ethylcellulose | 30 mg |
| Unsaturated fatty acid glyceride | 2 mg |
| Titanium dioxide | 2 mg |
| Per one tablet | 300 mg |

DOSAGE FORM EXAMPLE 2

Granules

Granules were prepared in the conventional manner according to the following formulation.

| | |
|---|---|
| Compound 5 | 200 mg |
| Mannitol | 540 mg |
| Corn starch | 100 mg |
| Crystalline cellulose | 100 mg |
| Hydroxypropylcellulose | 50 mg |
| Talc | 10 mg |
| Per one wrapper | 1000 mg |

DOSAGE FORM EXAMPLE 3

Fine granules

Fine granules were prepared in the conventional manner according to the following formulation.

| | |
|---|---|
| Compound 6 | 200 mg |
| Mannitol | 520 mg |
| Corn starch | 100 mg |
| Crystalline cellulose | 100 mg |
| Hydroxypropylcellulose | 70 mg |
| Talc | 10 mg |
| Per one wrapper | 1000 mg |

DOSAGE FORM EXAMPLE 4

Capsules

Capsules were prepared in the conventional manner according to the following formulation.

| | |
|---|---|
| Compound 8 | 100 mg |
| Lactose | 50 mg |
| Corn starch | 47 mg |
| Crystalline cellulose | 50 mg |
| Talc | 2 mg |
| Magnesium stearate | 1 mg |
| Per one capsule | 250 mg |

DOSAGE FORM EXAMPLE 5

Syrup

A syrup was prepared in the conventional manner according to the following formulation.

| | |
|---|---|
| Compound 7 | 1 g |
| Purified sucrose | 60 g |
| Ethyl para-hydroxybenzoate | 5 mg |
| Butyl para-hydroxybenzoate | 5 mg |
| Flavor | suitable amount |
| Coloring matter | suitable amount |
| Purified water | suitable amount |
| Total amount | 100 ml |

DOSAGE FORM EXAMPLE 6

Injection

An injection was prepared in the conventional manner according to the following formulation.

| | |
|---|---|
| Compound 10 | 100 mg |
| Distilled water for injection | suitable amount |
| Per one ampoule | 2 ml |

DOSAGE FORM EXAMPLE 7

Suppositories

Suppositories were prepared in the conventional manner according to the following formulation.

| | |
|---|---|
| Compound 12 | 100 mg |
| Witepsol W-35 | 1400 mg |
| (registeredtrademark; a mixture of mono-, di- and triglycerides of saturated fatty acids consisting of lauric acid to stearic acids; product of Dynamit Nobel Co., Ltd.) | |
| Per one suppository | 1500 mg |

Pharmacological Tests (1) Cyclooxygenase inhibiting effect

This assay was carried out by the method described in Russell J. Taylor et al., Biochem. Pharmacol., 25, 2479–2484 (1976).

$^{14}$C-arachidonic acid was reacted with seminal vasicular gland microsomes and the test drugs at various concentrations over a predetermined period of time and the obtained prostaglandin $E_2$ was separated by thin layer chromatography. The radioactivity of prostaglandin $E_2$ was determined by liquid scintillation counter. The $IC_{50}$ values were calculated by the comparison with the radioactivity of the control.

(2) 5-Lipoxygenase inhibiting activity

This assay was carried out by the method described in Kenkichi Ochi et al., J. Biol. Chem., 258, 5754–5758 (1983).

Casein was injected into the abdominal cavity of a guinea pig, and the polymorphonuclear leucocytes were collected and the cytosol fraction was obtained as an enzyme source. $^{14}$C-arachidonic acid was reacted with the enzyme and the test drug at various concentrations over a predetermined period of time. The obtained 5-hydroxyeicosatetraenoic acid was separated by thin layer chromatography and the radioactivity was determined. The IC$^{50}$ values were calculated by the comparison with the radioactivity of the control.

The results of the above tests (1) and (2) are shown below in Table 2.

TABLE 2

| Compound No. | IC$_{50}$ (μM) | |
|---|---|---|
| | cyclooxygenase | 5-Lipoxygenase |
| 4 | 0.066 | 0.062 |
| 5 | 0.1 | 0.113 |
| 6 | 2.6 | 0.1 |
| 7 | 2.6 | 0.11 |
| 8 | 1.5 | 0.086 |
| 10 | 0.10 | 0.67 |
| 12 | 0.015 | 0.24 |
| 13 | 0.01 | 0.05 |
| 14 | <0.01 | 0.13 |
| 15 | 0.05 | 0.11 |
| 16 | 0.29 | 0.23 |
| 38 | 0.14 | 0.055 |
| 39 | 1.31 | 0.18 |
| 40 | 0.24 | 3.03 |
| 46 | 0.28 | 0.39 |
| 48 | 0.03 | 0.63 |

The results of Table 2 shows that the compounds of the present invention potently inhibit both cyclooxygenase and lipoxygenase.

We claim:

1. An isoxazole derivative represented by the general formula (1) or a salt thereof,

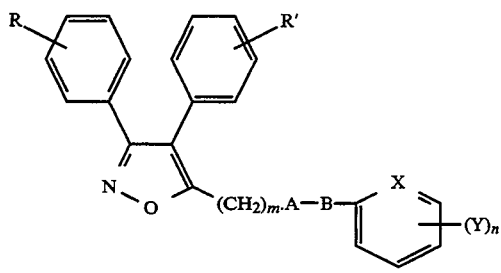

wherein R and R$^1$ are the same or different and each is a hydrogen atom, a lower alkyl group, a lower alkoxy group or a halogen atom; m is 0 to 5; A is —NH—, —O— or a direct bond; B is —C(=Z)—NH—, —C(= Z)—(CH=CH)$_l$— or —CH=CH— (wherein Z is an oxygen or sulfur atom and l is 0 to 2; provided that when m is 0 and A is a direct bond and Z is an oxygen atom, l is not 0); X is a nitrogen or carbon atom; n is 0 to 3; and Y is a hydroxy group, a lower alkoxy group, a lower alkyl group, a lower alkoxycarbonyloxy group, a lower alkoxycarbonylmethyloxy group, a carboxylmethyloxy group, an amino acid residue which may have a protective group, a lower alkylcarbonyloxy group, a pyridylcarbonyloxy group, a dimethylaminophenylcarbonyloxy group or a di-lower-alkyl phosphate residue; provided that when n is 2 or 3, the two or three Ys are the same or different and each is one of the groups mentioned above, that when n is 2 or more, two Ys may form a methylenedixoy group, that when X is a nitrogen atom, n is 0 and that when A is —NH—, m is 1 to 5.

2. The isoxazole derivative or salt thereof according to claim 1 wherein R and R' are the same or different and each is a lower alkoxy group or a halogen atom.

3. The isoxazole derivative or salt thereof according to claim 1 wherein m is 0 to 3.

4. The isoxazole derivative or salt thereof according to claim 1 wherein m is 1 to 3.

5. The isoxazole derivative or salt thereof according to claim 1 wherein A is —NH— or a direct bond.

6. The isoxazole derivative or salt thereof according to claim 1 wherein B is —C(=Z)—(CH=CH)$_l$— (wherein Z is an oxygen or sulfur atom and l is 1 or 2).

7. The isoxazole derivative or salt thereof according to claim 1 wherein Y is a hydroxy group, a lower alkoxy group, a lower alkyl group or a lower alkoxycarbonyloxy group and n is 2 or 3.

8. The isoxazole derivative or salt thereof according to claim 1 wherein X is a carbon atom.

9. The isoxazole derivative or salt thereof according to claim 1 wherein m is 0 to 3, A is —NH— or a direct bond, B is —C(=Z)—(CH=CH)$_l$— (wherein Z is an oxygen or sulfur atom and l is 1 or 2), Y is a hydroxy group, a lower alkoxy group, a lower alkyl group or a lower alkoxycarbonyloxy group, n is 2 or 3 and X is a carbon atom.

10. The isoxazole derivative or salt thereof according to claim 1 wherein R and R' are the same or different and each is a lower alkoxy group or a halogen atom, m is 1 to 3, A is —NH— or a direct bond, B is —C(= Z)—(CH=CH)$_l$— (wherein Z is an oxygen or sulfur atom and l is 1 or 2), Y is a hydroxy group, a lower alkoxy group, a lower alkyl group or a lower alkoxycarbonyloxy group, n is 2 or 3 and X is a carbon atom.

11. A composition for inhibiting lipoxygenase comprising an effective amount of the isoxazole derivative as defined in claim 1 and a pharmaceutically acceptable carrier therefor.

12. A composition for inhibiting 5-lipoxygenase comprising an effective amount of the isoxazole derivative as defined in claim 1 and a pharmaceutically acceptable carrier therefor.

13. A composition for inhibiting cyclooxygenase comprising an effective amount of the isoxazole derivative as defined in claim 1 and a pharmaceutically acceptable carrier therefor.

14. A method for inhibiting lipoxygenase which comprises administering to a patient an effective amount of the isoxazole derivative as defined in claim 1.

15. A method for inhibiting 5-lipoxygenase which comprises administering to a patient an effective amount of the isoxazole derivative as defined in claim 1.

16. A method for inhibiting cyclooxygenase which comprises administering to a patient an effective amount of the isoxazole derivative as defined in claim 1.

* * * * *